US009241454B2

(12) United States Patent
Denarie et al.

(10) Patent No.: US 9,241,454 B2
(45) Date of Patent: Jan. 26, 2016

(54) LIPOCHITO-OLIGOSACCHARIDES STIMULATING ARBUSCULAR MYCORRHIZAL SYMBIOSIS

(75) Inventors: Jean Denarie, Castanet-Tolosan (FR); Fabienne Maillet, Pompertuzat (FR); Véréna Poinsot, Lacroix-Falgarde (FR); Olivier Andre, Toulouse (FR); Guillaume Becard, Odars (FR); Monique Gueunier, Saint Orens de Gameville (FR); Laurence Cromer, Malakoff (FR); Alexandra Haouy, Chauvigny (FR); Delphine Giraudet, Paimpol (FR)

(73) Assignees: INSTITUT NATIONAL DE LA RECHERCHE AGRONOMIQUE, Paris (FR); CENTRE NATIONAL DE LA RECHERCHE SCIENTIFIQUE (C.N.R.S.), Paris (FR); UNIVERSITE PAUL SABATIER, Toulouse (FR)

( * ) Notice: Subject to any disclaimer, the term of this patent is extended or adjusted under 35 U.S.C. 154(b) by 150 days.

(21) Appl. No.: 13/126,942

(22) PCT Filed: Oct. 28, 2009

(86) PCT No.: PCT/IB2009/007492
§ 371 (c)(1),
(2), (4) Date: Aug. 26, 2011

(87) PCT Pub. No.: WO2010/049817
PCT Pub. Date: May 6, 2010

(65) Prior Publication Data
US 2011/0301032 A1 Dec. 8, 2011

(30) Foreign Application Priority Data

Oct. 29, 2008 (WO) .................. PCT/IB2008/003484

(51) Int. Cl.
*A01N 43/04* (2006.01)
*A01H 3/04* (2006.01)
*A01H 17/00* (2006.01)
*A01N 43/16* (2006.01)
*A01N 63/04* (2006.01)
*C07H 13/06* (2006.01)
*C08B 37/08* (2006.01)
*C12N 15/82* (2006.01)

(52) U.S. Cl.
CPC .................. *A01H 3/04* (2013.01); *A01H 17/00* (2013.01); *A01N 43/16* (2013.01); *A01N 63/04* (2013.01); *C07H 13/06* (2013.01); *C08B 37/003* (2013.01); *C12N 15/8291* (2013.01)

(58) Field of Classification Search
CPC ......... A01H 3/04; A01H 17/00; A01N 43/16; A01N 63/04
USPC ........................................................ 514/55
See application file for complete search history.

(56) References Cited

U.S. PATENT DOCUMENTS

| 5,175,149 | A | 12/1992 | Stacey et al. |
| 5,321,011 | A | 6/1994 | Stacey et al. |
| 5,549,718 | A | 8/1996 | Lerouge et al. |
| 6,979,664 | B1 * | 12/2005 | Smith et al. ................... 504/117 |
| 7,619,076 | B2 | 11/2009 | Beau et al. |
| 8,013,132 | B2 | 9/2011 | Beau et al. |

FOREIGN PATENT DOCUMENTS

| JP | 09 241112 | 9/1997 |
| WO | WO 00/04778 | 2/2000 |
| WO | WO 2005/063784 | 7/2005 |
| WO | WO 2008/085958 | 7/2008 |
| WO | WO 2010/049817 | 5/2010 |

OTHER PUBLICATIONS

Spaink, H.P., Sheeley, D.M., van Brussel, A.A.N., Glushka, J., York, W.S., Tak, T., Geiger, O., Kennedy, E.P., Reinhold, V.N., Lugtenberg, B.J.J. (1991) A novel highly unsaturated fatty acid moiety of lipo-oligosaccharide signals determines host specificity of Rhizobium. Nature, vol. 354, p. 125-130.*
Folch-Mallol, J.L., et al. (1996) Characterization of Rhizobium tropici CIAT899 Nodulation Factors: The Role of nodH and nodPQ Genes in Their Sulfation. Molecular Plant-Microbe Interactions, vol. 9, No. 3, p. 151-163.*
Akiyama et al. (Jun. 2005) "Plant sesquiterpenes induce hyphal branching in arbuscular mycorrhizal fungi," *Nature*, 435:824-827.
Ardourel et al. (Oct. 1994) "Rhizobium meliloti lipooligosaccharide nodulation factors: Different structural requirements for bacterial entry into target root hair cells and induction of plant symbiotic developmental responses," *Plant Cell* 6:1357-1374.
Besserer et al. (Jun. 27, 2006) "Strigolactones stimulate arbuscular mycorrhizal fungi by activating mitochondria," *PLoS Biol.* 4(7):e226.
Boone et al. (1999) "Structural characterisation of lipo-chitin oligosaccharides isolated from Bradyrhizobium aspalati, microsymbionts of commercially important South African legumes" *Carbohydrate Res.* 317(1-4):155-163.
Buhler, N.F. (2007) "Gene induction during plant-microbe interactions: The role of chitinases during fungal infection and the investigation of mycorrhiza-induced genes in the model plant M. truncatula" Philosophisch-Naturwissenschaftlichen Fakultat der Universitat Basel, Basel.
Catford et al. (May 2003) "Suppression of arbuscular mycorrhizal colonization and nodulation in split-root systems of alfalfa after pre-inoculation and treatment with Nod factors," *J. Exp. Bot.* 54(386)1481-1487.
Catoira et al. (2000) "Four genes of *Medicago truncatula* controlling components of a Nod factor transduction pathway," *Plant Cell* 12:1647-1666.
Cohn et al. (Mar. 1, 1998) "Legume nodule organogenesis" *Trends Plant Sci.* 3(3):105-110.
Debelle et al. (Feb. 2007) "Calcium and Nod Signaling," *Med. Sci.* 23(2):130-132.

(Continued)

*Primary Examiner* — Scarlett Goon
(74) *Attorney, Agent, or Firm* — Lathrop & Gage LLP

(57) ABSTRACT

The invention relates to lipochitooligosaccharides obtainable from arbuscular mycorrhizal fungi, and which are useful for stimulating arbuscular mycorrhizal symbiosis, and lateral root formation.

17 Claims, 16 Drawing Sheets

(56) References Cited

OTHER PUBLICATIONS

Figure 1:
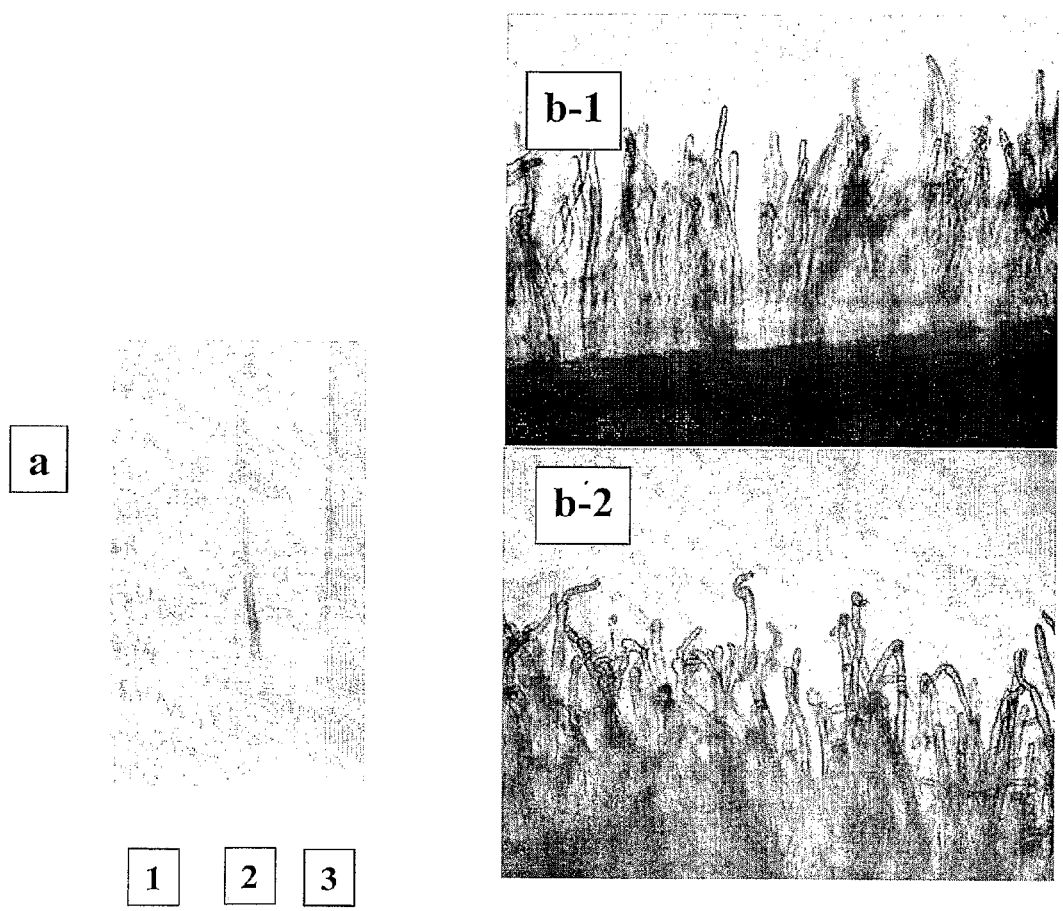

Denarie et al. (Jul. 1, 1996) "Rhizobium lipo-chitooligosaccharide nodulation factors: Signaling molecules mediating recognition and morphogenesis," *Ann. Rev. Biochem.* 65:503-535.
D'haeze et al. (2002) "Nod factor structures, responses, and perception during initiation of nodule development," *Glycobiology* 12(6):79R-105R.
Grenouillat et al. (2004) "Simple synthesis of nodulation-factor analogues exhibiting high affinity towards a specific binding protein," *Angew Chem Int Ed Engl.* 43:4644-4646.
Groves et al. (Jan. 1, 2005) "The Relative Orientation of the Lipid and Carbohydrate Moieties od Lipochitooligosaccharides Related to Nodulation Factors Depends on Lipid Chain Saturation," *Org. Biomol. Chem.* 3:1381-1386.
Hogg et al. (Jan. 2006) "The DMI1 and DMI2 early symbiotic genes of Medicago truncatula are required for a high-affinity nodulation factor-binding site associated to a particulate fraction of roots" *Plant Physiol.* 140(1):365-373.
International Search Report and Written Opinion, Corresponding to International Application No. PCT/IB2009/007492, Mailed Jul. 13, 2010.
John et al. (Mar. 1, 1997) "Cell signaling by oligosaccharides," *Trends Plant Sci.* 2(3):111-115.
Kosuta et al. (Mar. 2003) "A diffusible factor from arbuscular mycorrhizal fungi induces symbiosis-specific MtENOD11 expression in roots of Medicago truncatula," *Plant Physiol.*, 131: 952-962.
Lopez-Iara et al. (1995) "Structural identification of the lipo-chitin oligosaccharide nodulation signals of Rhizobium loti," *Mol. Microbiol.* 15(4):627-638.
Lum et al. (Dec. 2002) "Roots and their symbiotic microbes: Strategies to obtain nitrogen and phosphorus in a nutrient-limiting environment," *J. Plant Growth Reg.* 21(4):368-382.
Mathesius, U. (Aug. 1, 2003) "Conservation and divergence of signaling pathways between roots and soil microbes—the Rhizobium-legume symbiosis compared to the development of lateral roots, mycorrhizal interactions and nematode-induced galls" *Plant Soil* 255(1):105-119.
Nagahashi et al. (Dec. 1, 2000) "Partial separation of root exudate components and their effects upon the growth of germinated spores of AM fungi" *Mycological Res.* 104(12):1453-1464.
Navazio et al. (Jun. 2007) "A diffusible signal from arbuscular mycorrhizal fungi elicits a transient cytosolic calcium elevation in host plant cells," *Plant Physiol.* 144:673-681.
Ohsten-Rasmussen et al. (Web Release Jun. 9, 2004) New access to lipo-chitooligosaccharide nodulation factors. *Org. Biomol. Chem.* 2:1908-1910.
Olah et al. (2005) "Nod factors and a diffusible factor from arbuscular mycorrhizal fungi stimulate lateral root formation in Medicago truncatula via the DMI1/DMI2 signaling pathway," *Plant J.* 44:195-207.
Oldroyd, G. (Jun. 1, 2001) "Dissecting symbiosis: Developments in Nod factor signal transduction" *Ann. Botany* 87(6):709-718.
Olsthoorn et al. (1998) "Novel Branched Nod Factor Structure Results from α-(1,3) Fucosyl Transferase Activity: The Major Lipo-Chitin Oligosaccharides from Mesorhizobium loti Strain NZP2213 Bear an α-(1,3) Fucosyl Substituent on a Nonterminal Backbone Residue" Biochemistry 37(25):9024-9032.
Orgambide et al. (1995) "Structurally Diverse Chitolipooligosaccharide Nod Factors Accumulate Primarily in Membranes of Wild Type Rhizobium leguminosarum biovar trifolii" *Biochemistry* 34(11):3832-3840.

Pacios-Bras et al. (2002) "Novel 5-9 lipochitin oligosaccharide structures produced by Rhizobium etli KIM5s" *Carbohydrate Res.* 337(13):1193-1202.
Prome et al. (Sep. 1, 2002) "The pivotal role of tandem mass spectrometry in structural determinations of Nod factors produced by Rhizobia- Nod factors produced by wild-type strains of Mesorhizobium huakii and Rhizobium sp. mus10" *Int. J. Mass Spectrom.* 219(3):703-716.
Renier et al. (Jun. 1, 2008) "Symbiotic properties of Methylobacterium nodulans ORS 2060[7]: A classic process for an atypical symbiont," *Soil Biol. Biochem.* 40(6):1404-1412.
Samain et al. (1999) "Production of O-acetylated and sulphated chitooligosaccharides by recombinant *Escherichia coli* strains harboring different combinations of *nod* genes," *J. Biotechnol.* 72:33-47.
Samain et al. (Jul. 11, 1997) "Gram-scale synthesis of recombinant chitooligosaccharides in *Escherichia coli*," *Carbohydrate Res.* 302:35-42.
Schultze et al. (1992) "Rhizobium-Meliloti Produces a Family of Sulfated Lipooligosaccharides Exhibiting Different Degrees of Plant Host Specificity," *Proc. Nat. Acad. Sci. USA* 89(1):192-196.
Smit et al. (Jun. 17, 2005) "NSP1 of the GRAS protein family is essential for rhizobial Nod factor-induced transcription," *Science* 308:1789-1791.
Stacey et al. (Web Release Feb. 2, 2006) "Genetics and functional genomics of legume nodulation," *Curr. Opin. Plant Biol.* 9:110-121.
Weidmann et al. (2004) "Fungal elicitation of signal transduction-related plant genes precedes mycorrhiza establishment and requires the dmi3 gene in Medicago truncatula," *Mol. Plant Microbe Interact.* 17(12):1385-1393.
Xie et al. (Jun. 1998) "Nod factors and tri-iodobenzoic acid stimulate mycorrhizal colonization and affect carbohydrate partitioning in mycorrhizal roots of Lablabpurpureus" *New Phytologist* 139(2):361-366.
Xie et al. (1995) "Rhizobial nodulation factors stimulate mycorrhizal colonization of nodulating and nonnodulating soybeans" *Plant Phys.* 108(4):1519-1525.
Yang et al. (Oct. 1999) "Structure of the Mesorhizobium huakuii and Rhizobium galegae Nod factors: A cluster of phylogenetically related legumes are nodulated by rhizobia producing Nod factors with alpha,beta-unsaturated N-acyl substitutions" *Mol. Microbiol.* 34(2):227-237.
Demont-Caulet et al. (1999), "Nodule-Inducing Activity of Synthetic *Sinorhizobium meliloti* Nodulation Factors and Related Lipo-Chitooligosaccharides on Alfalfa. Importance of the Acyl Chain Structure," Plant Physiology, May 1999, vol. 120, pp. 83-92.
Lerouge et al. (1990), "Symbiotic host-specificity of *Rhizobium meliloti* is determined by a sulphated and acylated glucosamine oligosaccharide signal," Nature, vol. 344, pp. 781-784.
Price et al. (1992), "Broad-host-range *Rhizobium* species strain NGR234 secretes a family of carbamoylated, and fucosylated, nodulation signals that are 0-acetylated or sulphated," Molecular Microbiology (1992) 6(23), 3575-3584.
Demont-Caulet et al. (1999) "Nodule-Inducing Activity of Synthetic Sinorhizobium meliloti Nodulation Factors and Related Lipo-Chitooligosaccharides on Alfalfa. Importance of the Acyl Chain Structure," Plant Physiology, vol. 120: 83-92.
Poupot R. et al. (1993) "Nodulation Factors from *Rhizobium tropici* are Sulfated or Nnnsulfated Chitopentasaccharides Containing an N-Methyl-N-acylglucosaminyl Terminus" Biochemistry 32:10430-10435.
Waelkens et al. (1995) "The nodS Gene of *Rhizobium tropici* Strain CIAT899 is Necessary for Nodulation on *Paseolus vulgaris* and on Leucaena leucocephala" Mol. Plant-Microbe Interactions, vol. 8(1):147-154.

* cited by examiner a b a b

LIPOCHITO-OLIGOSACCHARIDES STIMULATING ARBUSCULAR MYCORRHIZAL SYMBIOSIS

CROSS-REFERENCE TO RELATED APPLICATIONS

This application is a U.S. National Stage application of international application PCT/IB2009/007492, filed in English on Oct. 28, 2009, which designates the United States, and which claims the benefit of PCT application No. PCT/IB2008/003484, filed in English on Oct. 29, 2008, which also designates the United States. Each of these applications is incorporated by reference herein in its entirety.

The invention relates to lipochito-oligosaccharides involved in arbuscular mycorrhizal symbiosis, and to their applications.

Arbuscular mycorrhizal (AM) fungi have established symbiotic associations with plant roots for over 400 million years, since the appearance of the earliest land plants, suggesting that AM fungi assisted plants in their colonization of land (Remy et al., 1994). This group of fungi, recently renamed Glomeromycota, is one of the most widely distributed and AM associations are widely distributed throughout the plant kingdom including angiosperms, gymnosperms, pteridophytes and some bryophytes (Smith and Read, 2008). Among the angiosperms, at least 80% of the species can form AM symbioses, the only major exceptions being Brassicaceae and Chenopodiaceae. AM fungi are able to transfer rare or poorly soluble mineral nutrients such as phosphorus, zinc and copper from the soil to the plant, which in turn provides carbohydrates to the fungus. This exchange of nutrients can be of critical importance when soil fertility and water availability are low, conditions that severely limit agricultural production in most parts of the world (Smith and Read, 2008).

Another known symbiotic association between plants and soil microorganisms is the rhizobial symbiosis. In contrast with the arbuscular mycorrhizal symbiosis, which is broadly distributed among plants, the rhizobial symbiosis is restricted to legumes, and instead of fungi, it involves nitrogen-fixing bacteria collectively called rhizobia, which belong to several genera including *Rhizobium, Bradyrhizobium, Azorhizobium*, and *Sinorhizobium*. The rhizobial symbiosis results in the formation of specific structures, the nodules, on the roots of the legume host. Nodules provide an appropriate environment for rhizobia, allowing them to fix molecular nitrogen and to provide combined nitrogen to the legume host. The initiation of the *Rhizobium*-legume association depends on symbiotic signals that are produced by both symbiotic partners. The signals released by the plant are usually flavonoids excreted in root exudates. These flavonoids interact with rhizobial transcription factors of the NodD family, which activate the transcription of nodulation (nod) genes involved in the production of the bacterial signaling molecules termed Nod factors (Denarie et al., 1996). Nod factors share a common basic structure consisting of a chitin backbone of four or five beta-1,4-linked N-acetylglucosamine residues, N-acylated at the non-reducing end with a fatty acid group of variable length and degree of unsaturation. This basic structure can be further N-methylated at the nonreducing end, and can also be O-substituted at the non-reducing end and/or at the reducing end. This variety of substituents provides a broad diversity of Nod factors with different structures (for the description of diverse structures of Nod factors see Dénarié et al., 1996; D'Haeze et al., 2002). The specificity within the legume/rhizobial interaction (i.e. a given species of rhizobia forms nodules on certain species of legumes) is the result of this diversity.

Genetic dissection of the pathway involved in Nod factor signaling in roots of the model legume *Medicago truncatula* has identified a number of genes involved in this pathway (Stacey et al., 2006). There is growing evidence that the Nod factor receptors are receptor-like kinases with extracellular sugar-binding LysM domains, such as those encoded by the NFP and LYK3 genes of *M. truncatula*. The interaction of a Nod factor with its receptor induces a downstream signaling cascade, including the rapid influx of calcium ions, calcium spiking, and expression of specific nodulin genes. These downstream events involve in particular genes encoding proteins involved in calcium signaling, such as DMI1, DMI2 and DMI3 of *M. truncatula* which encode respectively a cation channel, a leucine rich-repeat receptor-like kinase, and a $Ca^{2+}$/calmodulin-dependent protein kinase, and genes encoding proteins involved in the control of gene expression, such as NSP1 and NSP2 which encode transcription factors.

Although AM fungi are both agriculturally and ecologically extremely important, the cellular and molecular mechanisms which control the formation of the mycorrhizal symbiosis, are far less known than those involved in rhizobial symbiosis.

It has been shown in *M. truncatula* that the nodulation and mycorrhizal programs share at least three components (Catoira et al. 2000), namely the products of the DMI1, DMI2 and DMI3 genes involved in calcium signaling.

However, the events taking place upstream and downstream this calcium signaling are still poorly characterized in the case of the arbuscular mycorrhizal symbiosis, in particular those involved in early signaling and leading to the recognition between the plant and the fungal partners. The study of these events has been hampered by the facts that the fungal partner is an obligatory symbiont which cannot be grown in pure culture in the absence of living plants, and by the absence of genetic tools available for this group of fungi (Harrison, 2005). However it has been shown recently that diffusible signals are exchanged between the symbionts prior to physical interaction. On the plant side, compounds of the apocarotenoid family, strigolactones, can be secreted in root exudates and stimulate ramifications in hyphae from AM fungi germinating spores, signaling a physiological switch to active pre-symbiotic fungal growth (Akiyama et al., 2005; Besserer et al., 2006). On the fungal side, the existence of diffusible compounds produced by AM fungi and able to activate plant responses associated to endomycorrhization program, has also been reported (Kosuta et al., 2003; Weidmann et al., 2004; Navazio et al., 2007). More specifically, a series of experiments performed with *M. truncatula* have recently shown that AM fungi produce diffusible compounds that are able to stimulate the expression of diverse plant responses. Three species of *Gigaspora* and one species of *Glomus* could trigger through a cellophane membrane the induction of expression of the MtENOD11 symbiotic gene in seedling roots (Kosuta et al., 2003). Three fungal pathogens did not elicit the same response, supporting the hypothesis that the response was induced by a specific AM fungal signal molecule. Similarly, an AM fungus, *Glomus intraradices*, was shown to activate through a membrane the transcription of plant genes whose expression depends on the DMI3 symbiotic gene (Weidmann et al. 2004). In addition, a diffusible signal from AM fungi was found to elicit a transient cytosolic calcium elevation in soybean cell cultures and the up-regulation of genes related to DMI1, DMI2 and DMI3 (Navazio et al., 2007).

Olah et al. (2005) reported that Nod factors from *Sinorhizobium meliloti*, the rhizobial symbiont of *M. truncatula*, were able to stimulate mycorrhization and lateral root formation in *M. truncatula*. The stimulation of lateral root formation was also observed with diffusible factors from arbuscular mycorrhizal fungi (Myc factors), but not with Nod factors) from rhizobial species (*Sinorhizobium fredii* and *Rhizobium leguminosarum*), which cannot nodulate *Medicago* sp. They also reported that all the genes of the Nod factor signaling pathway presently identified, including in particular the NFP gene encoding the putative Nod factor receptor, as well as the DMI3 and NSP1 genes were required for stimulation of lateral root formation by Nod factors, but not by Myc factors, which required only the DMI1 and DMI2 genes. On the basis of these observations, these authors proposed a model explaining the stimulation of mycorrhization and of lateral root formation in legumes by both Myc factors and Nod factors. According to this model, Myc factors and Nod factors, which were recognized by different cell surface receptors, activated a common DMI1/DMI2/DMI3 signalling pathway; in the case of Myc factors, DMI1 and DMI2 were sufficient for stimulation of lateral root formation, while DMI3 was required for stimulation of mycorrhization. Olah et al. also discussed the possible chemical nature of the Myc factors. They hypothesized that they were unlikely to be auxin-like compounds, since their effect on root development was different from the one observed with these compounds. They also suggested that their structure should be different from the structure of Nod factors, since they appeared to be discriminated by the NFP receptor.

Therefore, it appears that although the existence of diffusible "Myc factors" produced by AM fungi, and able to activate plant responses, is recognized in the art, the chemical nature of these factors has not been identified until now.

The inventors have now succeeded in purifying Myc factors from exudates from both mycorrhized roots and germinating spores of the AM fungus *Glomus intradices*. They have further determined their chemical structure, and shown that they efficiently stimulate root system development and root colonization by an AM fungus.

The Myc factors purified by the inventors are a mixture of sulfated and non-sulfated lipochito-oligosaccharides (LCOs); they share with the Nod factors a common basic chitin backbone of beta-1,4-linked N-acetylglucosamine residues, N-acylated at the non-reducing end with a fatty acid group. However the Myc factors have simpler structures than the Nod factors. The only O-substitution which is observed in Myc factors is O-sulfation at the reducing end of the molecule. No other O-substitutions such as O-carbamoyl at the non-reducing end, or O-fucosyl at the reducing end could be detected. The single N-substitution on the non-reducing terminal GlcNAc residue for Myc factors purified from *Glomus intradices* is the acylation by common fatty acids, mainly oleic (C18:1) and palmitic (C16:0) acids. In contrast the N-substitution of Nod factors is more complex. It is frequently a double substitution by an N-methyl group and an N-acyl group (frequently vaccenic acid), as in rhizobial strains that nodulate most tropical legumes and legumes of the Mimosoideae sub-family. N-methylation is specified by the widespread nodS rhizobial gene (Dénarié et al., 1996). Alternatively, N-acylation by a specific poly-unsaturated fatty acid is the rule among rhizobia that nodulate temperate legumes of the Galegoid clade (Dénarié et al., 1996). In fact, LCOs having a structure as simple as the Myc factors characterized by the inventors were not observed among the Nod factors synthesized by the various rhizobial strains studied so far (Dénarié et al., 1996; D'Haeze et al., 2002).

The invention provides a process for obtaining Myc factors from a fungus from the group Glomeromycota, wherein said process comprises obtaining exudates from plant roots mycorrhized with said fungus, or from germinating spores of said fungus, extracting said exudates with butanol, and recovering the butanol extract containing said lipochito-oligosaccharides.

According to a preferred embodiment of the invention, said process comprises the further steps of subjecting said butanol extract to solid phase extraction on a C18 reverse-phase, with successive washes at 20%, 50% and 100% acetonitrile and recovering the fraction eluted at 50% acetonitrile containing said Myc factors.

Still more preferably, said process comprises the further steps of subjecting said fraction eluted at 50% acetonitrile to reverse-phase high-performance liquid chromatography on a C18 reverse-phase column, using a linear gradient of 20% to 100% acetonitrile, and recovering the fraction eluted at 30-48% of acetonitrile which contains sulfated lipochito-oligosaccharides, and/or the fraction eluted at 64-72% of acetonitrile which contains non-sulfated lipochito-oligosaccharides.

According to a particular embodiment of the invention, said fungus from the group Glomeromycota is *Glomus intraradices*.

Fungal Myc factors can however also be extracted from other species of Glomeromycota producing them, using the extraction steps disclosed above, or variants thereof.

A "Myc factor" is herein defined a lipochito-oligosaccharide represented by the formula (I) below:

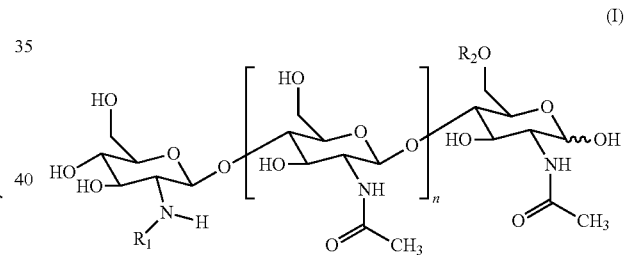

(I)

wherein n=0, 1, 2, 3, 4, or 5, preferably 2 or 3, $R_1$ represents a lipid substituent, containing 12 to 22, preferably 14 to 20 carbon atoms, which can be saturated, or mono-, di-, tri- tetra-, penta-, or hexaunsaturated, and $R_2$ represents H or $SO_3H$.

The lipid substituent $R_1$ is preferably a fatty acid chain. $R_1$ can also represent an aromatic analogue of a fatty acid chain, as in Nod factor analogues disclosed for instance by Grenouillat et al. (2004), or in PCT WO/2005/063784.

Advantageously, $R_1$ represents a chain of a fatty acid synthesized by) arbuscular mycorrhizal fungi, in particular a C16 or C18 fatty acid chain, saturated, or mono- or di-unsaturated. Preferably, when said fatty acid chain is unsaturated, it comprises at least one cis-unsaturation (for example the C18:1 oleic acid). By way of non-limitative examples of preferred fatty acid chains, one can mention C16:0, C18:0, C16:1ω5, C16:1ω7, C18:1ω5, C18:1ω7, C18:1ω9, 18:2ω6,9, C20:0 iso, C20:1ω9 and C20:4ω6,9,12,15.

Myc factors can further be characterized and also differentiated from lipochito-oligosaccharides of related structure such as Nod factors by their biological properties. These biological properties can be tested using appropriate bioassays. In particular, one can use bioassays based on the ability of the Myc factors to stimulate lateral root formation in the model legume *M. truncatula*. More specifically, while Myc factors share with Nod factors the ability to stimulate lateral root formation in wild-type plants but not in the symbiosis-defective mutants dmi1, dmi2 and dmi3, Myc factors are also able, unlike Nod factors, to stimulate lateral root formation in the symbiosis-defective mutant nsp1.

If wished, bioassays for differentiating non-sulfated Myc factors from sulfated Myc factors are also available (for instance if one wishes to separate in a fungal extract, fractions containing non-sulfated Myc factors from those containing sulfated Myc factors): for instance, sulfated Myc factors are able to induce the expression of the MtENOD11 gene in growing roots of *M. truncatula* while non-sulfated Myc factors are able to induce root hair branching in vetch.

Myc factors can be purified from fungi, as described above. They also be obtained by chemical synthesis and/or produced in genetically engineered bacterial cells. For instance, a chito-oligosaccharide backbone, sulfated or not, can be synthesised in recombinant bacteria, as disclosed for instance by Samain et al. (1997, 1999) for the synthesis of Nod factor precursors, and subsequently acylated on the free amine group of the non-reducing terminal sugar, as disclosed for instance by Ohsten Rasmussen et al. (2004). One can also use a mutant strain of a Rhizobiaceae bacterium producing Myc factors rather than Nod factors, for instance a strain genetically modified in order to express, among the structural genes of the Nod biosynthetic pathway, only those involved in the synthesis of the chito-oligosaccharide backbone and those involved in the N-acylation of the non-reducing terminal glucosamine by an appropriate C16 or C18 fatty acid, and optionally those involved in the O-sulfation of the reducing terminal glucosamine, as disclosed for instance by Ardourel et al. (1994), or Lugtenberg et al. (1995).

The invention also encompasses mixtures of different Myc factors of formula (I), and in particular mixtures of sulfated and non-sulfated Myc factors, comprising one or more lipo-chito-oligosaccharides of formula (I) wherein $R_2$ represents H, and one or more lipochito-oligosaccharides of formula (I) wherein $R_2$ represents $SO_3H$. The lipochito-oligosaccharides of said mixture may further differ between them by the number of N-acetylglucosamine residues and/or the nature of the substituent $R_1$ (for instance the length and/or the degree of unsaturation of the fatty acid chain).

Mixtures of Myc factors of the invention can for instance be obtained by extracting Myc factors from arbuscular mycorrhizal fungi, as described above, and recovering the fungal extract. They can also be obtained by producing separately the different Myc factors and mixing them.

Purified or synthetic lipochito-oligosaccharides and more specifically the purified or synthetic Myc factors of formula (I) or mixtures thereof described herein can be used to stimulate mycorrhization, and thus have a broad range of applications in agriculture, horticulture and forestry, for most cultivated plants which can establish mycorrhization, and therefore possess Myc factor receptors.

In addition to their use for stimulating the arbuscular mycorrhizal symbiosis, the purified or synthetic Myc factors or mixtures thereof can also be used:
- to stimulate the germination of seeds, which can be useful for seed treatment with a broad range of applications in agriculture, horticulture and forestry;
- to stimulate the root system development, which is beneficial to improve water and mineral nutrition.

They can be used for instance for treating seeds, or added to inoculants containing arbuscular mycorrhizal fungi, or added to the soil or the culture substrate of the plant. The purified or synthetic Myc factors of the invention can be used with any plant namely with plants which can establish mycorrhization, including as well legumes as non-legume plants, and including as well dicotyledons as monocotyledons, such as cereals. They can be used for plants grown under growth chamber, as well as in greenhouse or in field conditions.

They can also be used for stimulating mycorrhizal colonization in the production of mycorrhizal inoculants (i.e AM fungal spores or hyphae, or fragments of mycorrhized roots), as additive to the culture media which are used for the production of these inoculants by plants grown on soil or on hydroponic or aeroponic conditions, or by co-culture of mycorrhizal fungi with excised roots.

The invention also encompasses compositions containing purified or synthetic Myc factors or mixtures thereof, and an agriculturally suitable carrier. Compositions of the invention may also comprise mutant strains of Rhizobiaceae bacteria genetically modified in order to produce Myc factors rather than Nod factors, as described above. Preferred compositions are those containing a mixture of sulfated and non-sulfated Myc factors.

The Myc factors can optionally be combined with other active constituents, such as flavonoids, apocarotenoids such as strigolactones, or jasmonate which are plant compounds which have been reported to act as symbiotic signals (Harrison, 2005; Akiyama et al., 2005; Besserer et al., 2006).

The formulation of these compositions depends on the intended mode of application, (for instance coating seeds, adding to a culture medium for production of mycorrhizal inoculants, treating the plant of the soil). They can for instance be formulated as water-dispersible or water-soluble solids such as powders, granules, pellets, or films, as liquid) aqueous solutions, suspensions, or emulsions, or as gels.

According to a preferred embodiment, these compositions are associated with fungal and/or plant material, for instance with an inoculant of an arbuscular mycorrhizal fungus, or with seeds of a plant able to establish mycorrhization; advantageously, said seeds are coated with the composition.

Advantageously, the Myc factors are used in the composition at a concentration of $10^{-5}$ M to $10^{-12}$ M. When added to a culture medium for production of AM fungal spores, they can be used at a concentration of $10^{-6}$ M to $10^{-10}$ M, preferably at a concentration of $10^{-7}$ to $10^{-9}$ M in the medium. When used for seed treatment or for stimulating the root system development, they can be used at a concentration of $10^{-6}$ M to $10^{-10}$ M, preferably at a concentration of $10^{-7}$ to $10^{-9}$ M. When a mixture of sulfated and non-sulfated Myc factors is used, concentrations as low as $10^{-8}$ to $10^{-10}$ M can be used.

The invention will be understood more clearly with the aid of the additional description which refers to the examples below and to the appended drawings. It should be clearly understood, however, that these examples and drawings, are given solely as illustration of the subject of the invention and do not constitute in any manner a limitation thereof.

LEGENDS OF THE DRAWINGS

FIG. 1. Biological Assays Used to Detect AM Fungal Symbiotic Signals a. The MtENOD11 assay. Roots of transgenic *M. truncatula* Jemalong A17 seedlings carrying the reporter construct pMtENOD11-GUS. GUS activity is detected by histochemical staining with 5-bromo-4-chloro-3-indolyl-b-glucuronic.

(1) Control roots treated with acetonitrile 2.5%. (2) Fraction after SPE and elution with 50% acetonitrile diluted 40 times. (3) The same fraction with a further ten-fold dilution.

b. The VsHab assay. Root hairs of vetch (*Vicia sativa* subsp. *nigra*) observed under light microscope after staining with methylene blue. (1) Root hairs treated) with an inactive fraction are straight. (2) Root hairs treated with active fractions are clearly branched.

Figure 2:
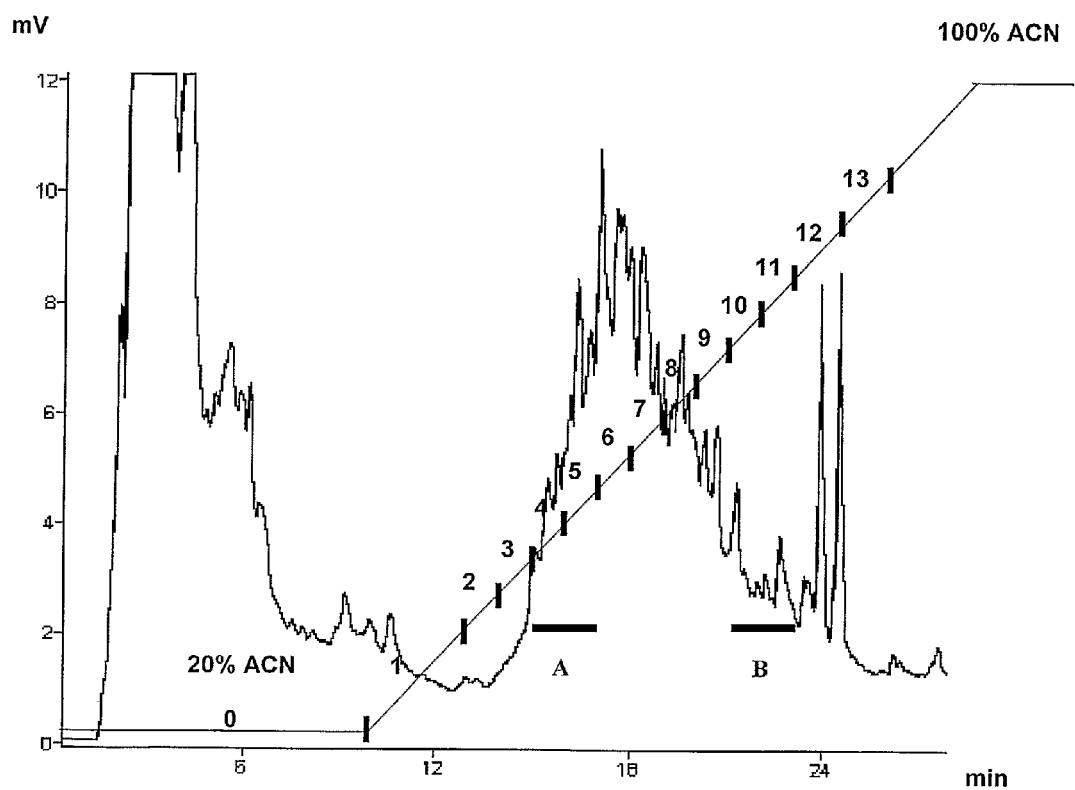

FIG. 2. Semi-Preparative C18 Reverse Phase HPLC Profile of Extracts from Mycorrhized Root Exudates.

The initial isocratic phase with 20% acetonitrile lasted 10 min and was followed by a 20-100% acetonitrile gradient for 20 min. The profile reveals the abundance of contaminating material present in mycorrhized root exudates. Fractions were collected every two minutes and were tested for biological activity on MtENOD11 and VsHab. Horizontal bars indicate the retention time of compounds in fraction A that are active on MtENOD11, and of compounds in fraction B, more hydrophobic, that are active on VsHab.

Figure 3:
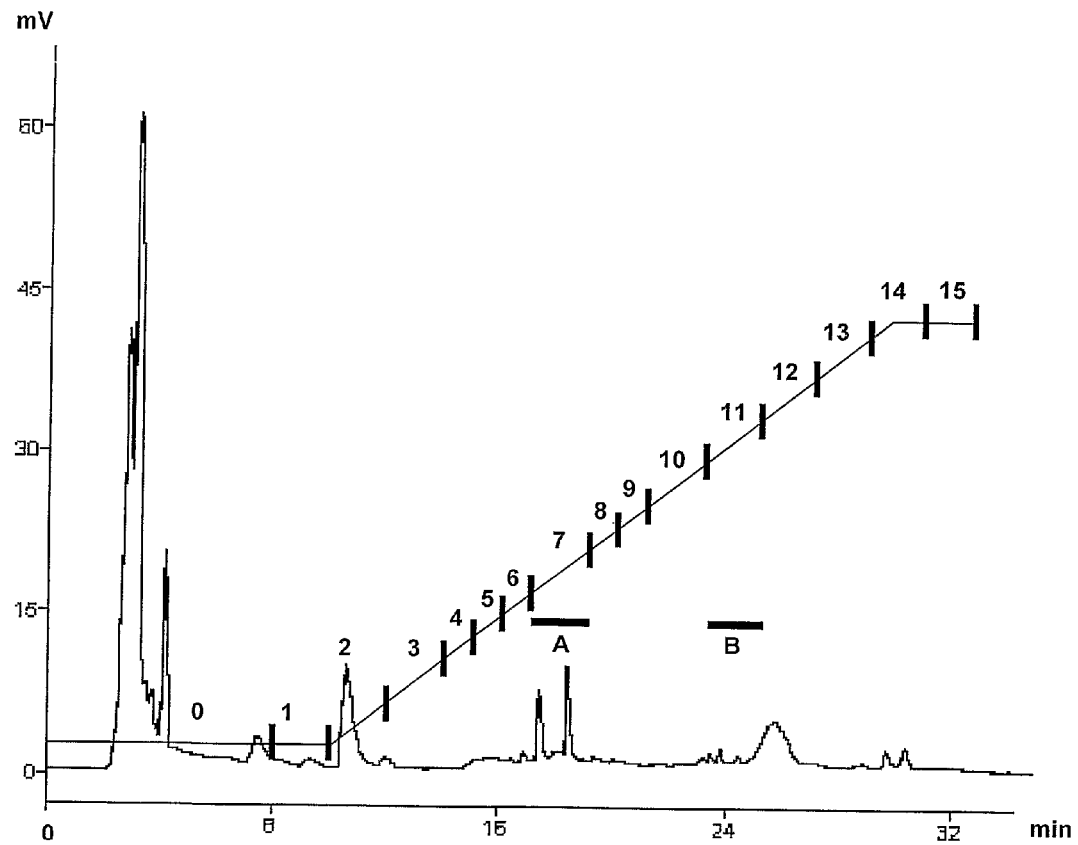

FIG. 3. Semi-Preparative C18 Reverse Phase HPLC Profile of Extracts from Germinating Spore Exudates.

The chromatographic conditions are the same as in FIG. 2. The profile reveals that spore exudates contain much less contaminating material than mycorrhized root exudates. Fractions were collected every two minutes and were tested for biological activity on MtENOD11 and VsHab. Horizontal bars indicate the retention time of compounds in fraction A that are active on MtENOD11, and of compounds in fraction B, more hydrophobic, that are active on VsHab.

Figure 4:
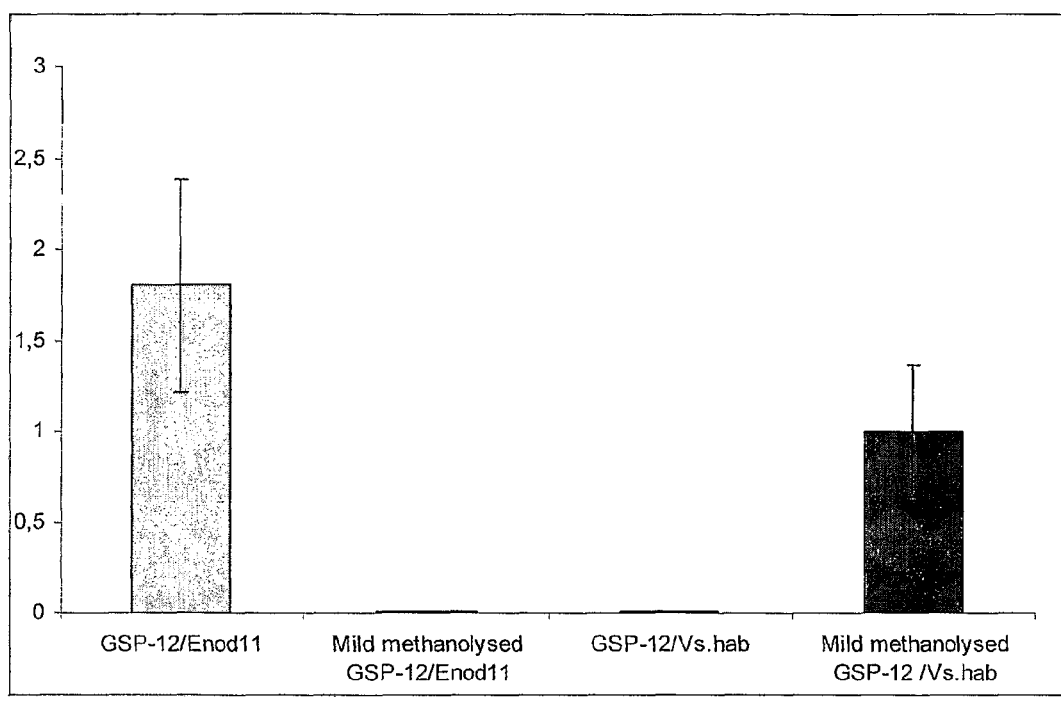

FIG. 4. Influence of Mild Methanolic Hydrolysis on the Biological Activity of Fraction A.

Mild methanolic hydrolysis has been reported to remove the sulfate moiety of sulfated LCOs without altering other structural features of these molecules. Fraction A collected during semi-preparative HPLC of germinating spore exudates was mildly hydrolyzed and tested for biological activity on MtENOD11 and VsHab assays. Biological activity is represented by vertical bars. Whereas unhydrolyzed fraction A is active on MtENOD11 and inactive on VsHab, the hydrolyzed fraction has lost activity on MtENOD11 and gained activity on VsHab. These data indicate that the biological activity of fraction A on the MtENOD11 assay is due to the presence of sulfated LCOs.

Figure 5:
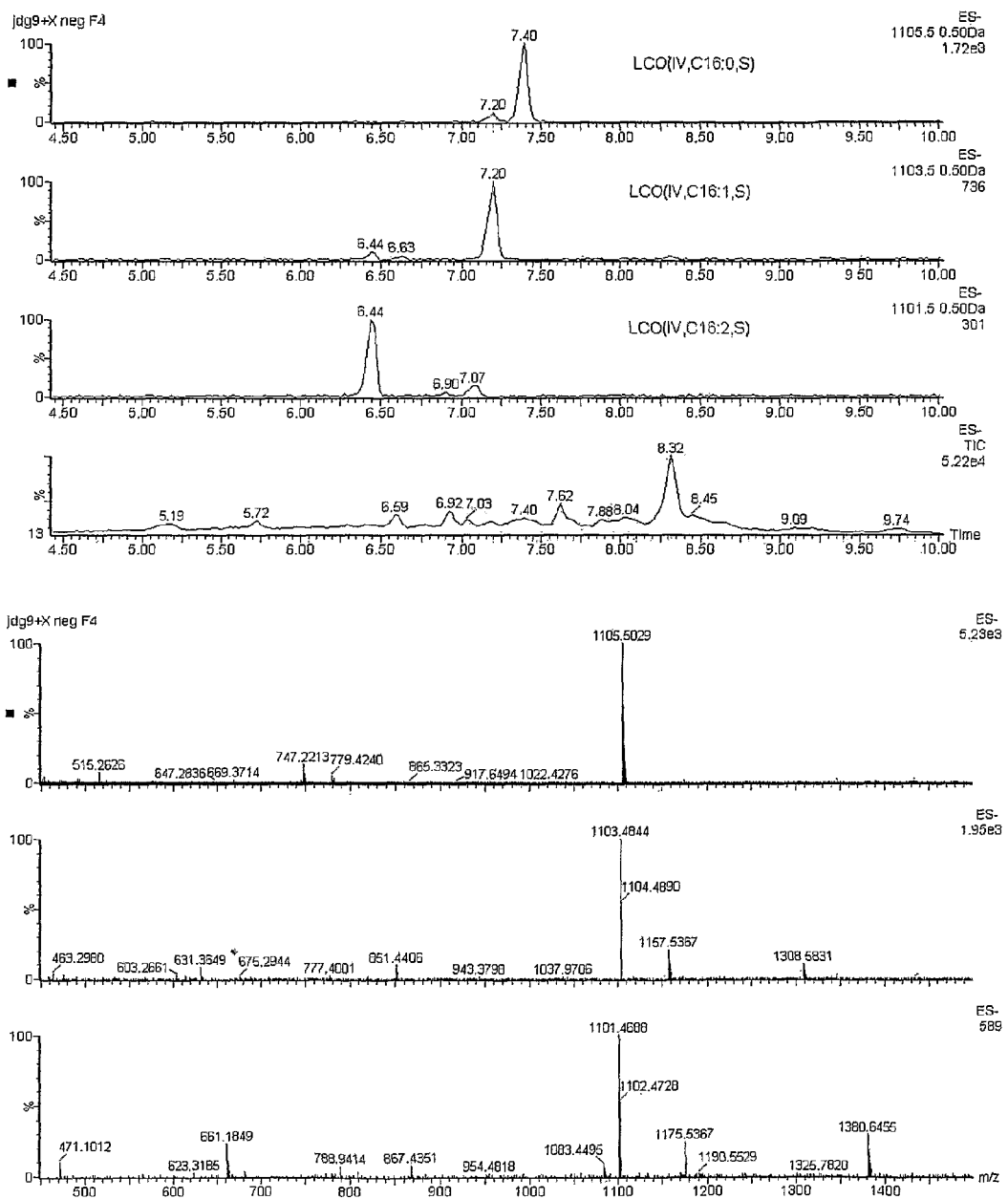

FIG. 5. Tetrameric Sulfated LCOs N-acylated by C16 Fatty Acids.

UPLC/MS traces, in the negative mode, of the fraction 4 isolated after semi-preparative C18 HPLC. Extracted ion currents corresponding to sulfated tetramers and corresponding spectra are given. This figure indicates that compounds responding at m/z 1101.5, 1103.5 and 1105.5 are effectively present in the samples. These m/z correspond to sulfated tetrameric LCOs N-acylated by C16:2, C16:1 and C16:0 respectively. Regarding the relative intensities of the three, it appears that 1105.5 (LCO-IV-C16:0) is the most abundant, followed by 1103.5 (LCO-IV-C16:1).

Figure 6:
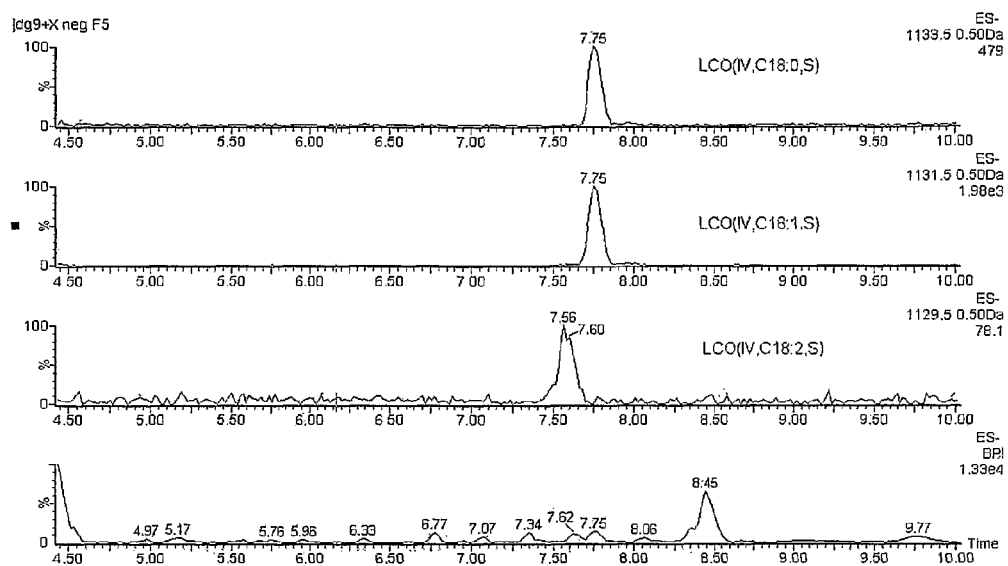
Figure 6:
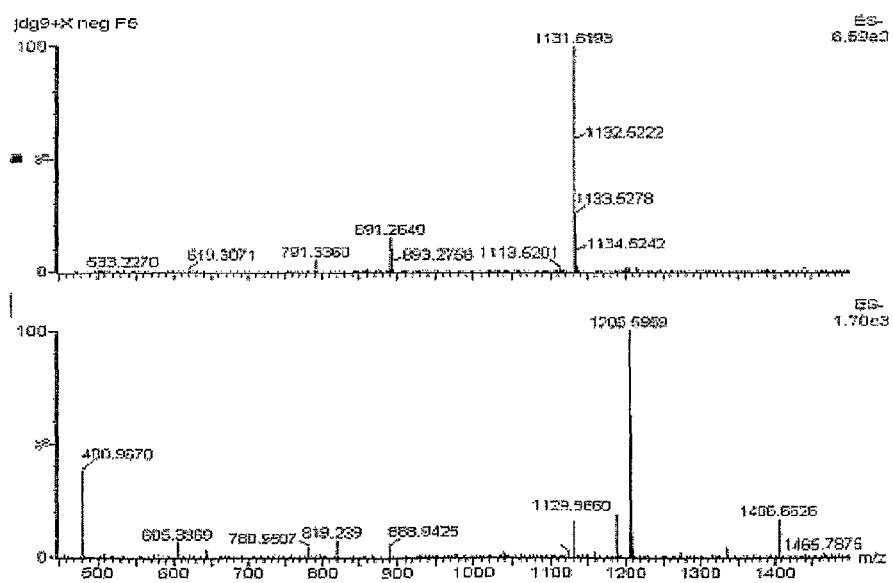

FIG. 6. Tetrameric Sulfated LCOs N-acylated by C18:1 Fatty Acid.)

UPLC/MS traces, in the negative mode of the fraction 5 isolated after semi-preparative C18 HPLC showing that the most abundant compound (m/z 1135.5) is N-acylated by a C18:1 fatty acid.

This profile also indicates that no LCO bearing a C18:0 fatty acid is present in this fraction (m/z 1133.5) as this ion is only the isotope +2 of the LCO bearing the C18:1 chain. As the second mass spectrum demonstrates, the di-unsaturated C18-LCO is a very minor compound.

Figure 7:
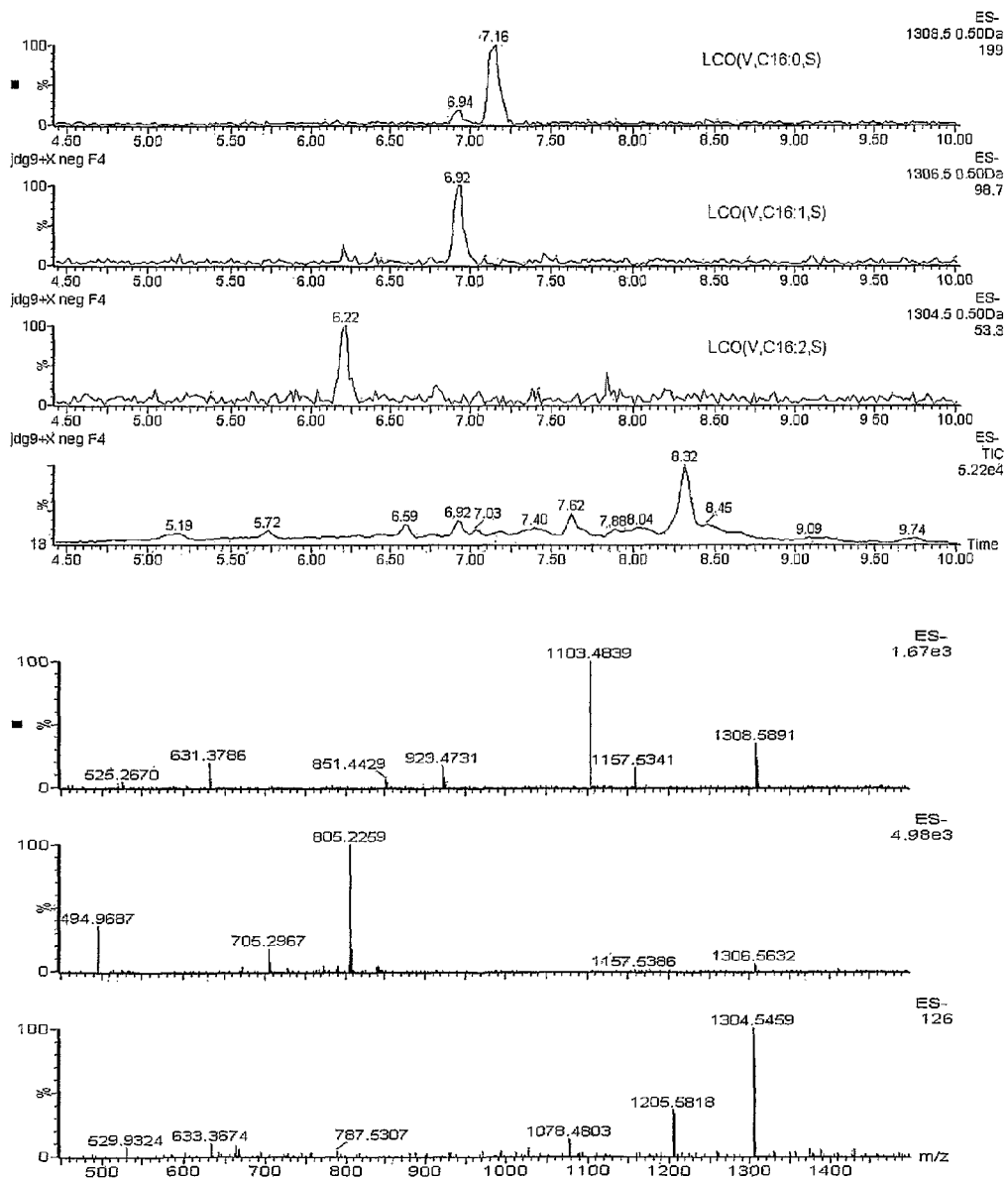

FIG. 7. Pentameric Sulfated LCOs N-acylated by C18:1 Fatty Acyl.

This profile shows that lipochitopentamers are also present, but compared to the corresponding tetramers (see FIG. 5) they are approximately 30 times less abundant. The LCO-V-C18:1 can be detected.

Figure 8:
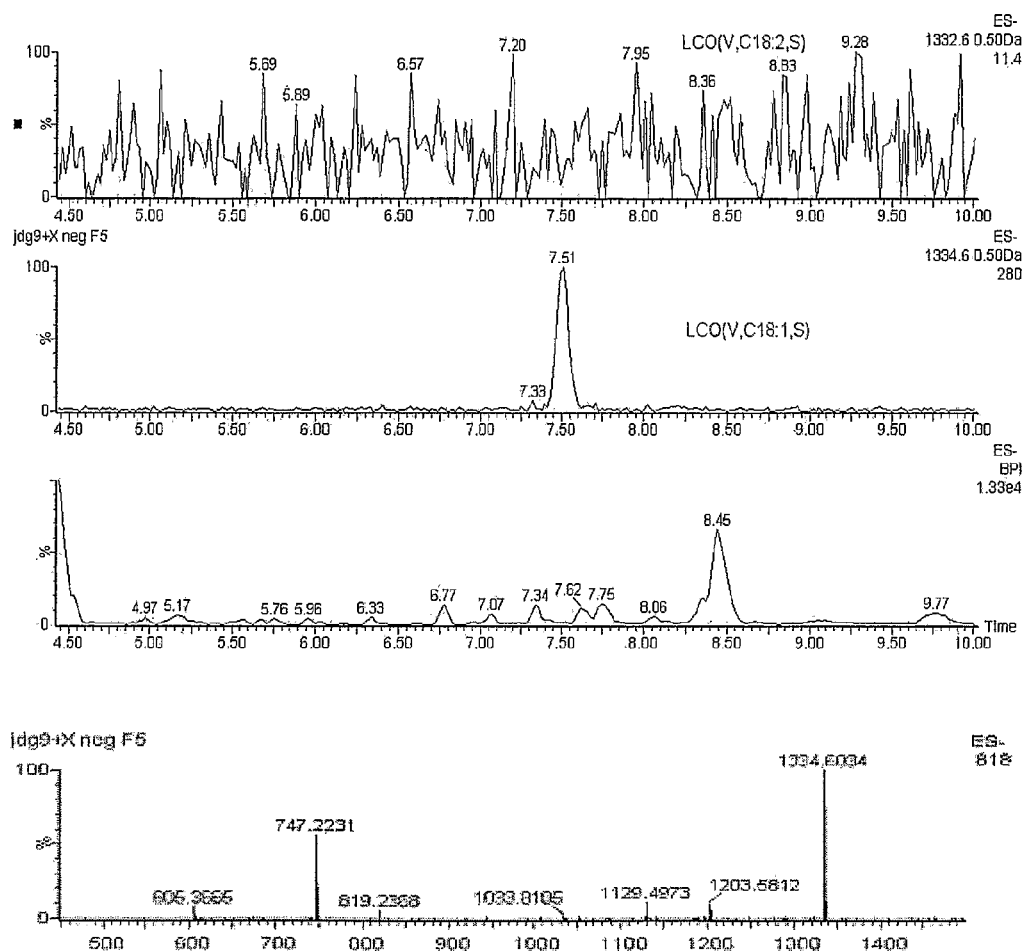

FIG. 8. Checking for the Presence or Absence of a Given Compound.

When the requested mass does not correspond to ions present in the sample the profile instead of giving a single peak gives a very large number of background peaks. The very complex profile obtained with ion current m/z 1332.6 demonstrates the absence of a C18:2 chitopentamer in the sample. In contrast, the clear single peak observed with ion current m/z 1334.6 clearly shows the presence of a C18:1 pentamer.

Figure 9:
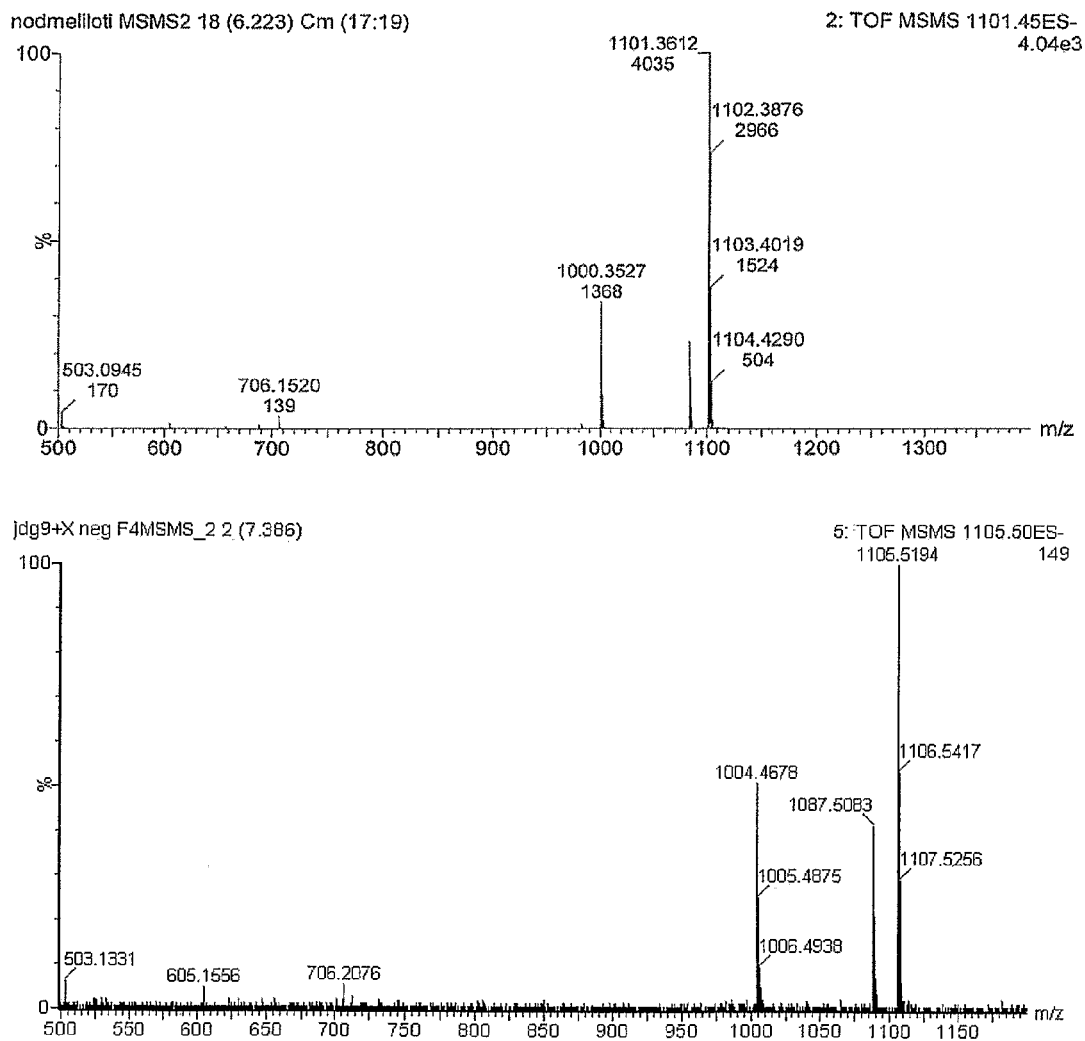

FIG. 9. Comparison of Fragmentation Pattern by MS/MS of Major Sulfated Myc Factor and *S. meliloti* Nod Factor Demonstrating the presence of compounds having the adequate mass at the expected HPLC retention time, is not sufficient to attest their structure. Therefore, we performed MS/MS analysis of the major sulfated Myc compound. This figure presents the comparison between the *S. meliloti* sulfated tetrameric Nod factor N-acylated by C16:2 in the negative mode MS/MS and the one recorded on the major tetrameric "Myc factor" present in the sample. Characteristic ions of the reducing end at m/z 503 ($Y_2$), 605 and 706 ($Y_3$) are clearly detected in both case as well as the characteristic neutral loss of 101 amu (intracyclic rupture) starting from the molecular ion. The perfect fit between the two fragmentation patterns indicates the structural affiliation of the two molecules.

Figure 10:
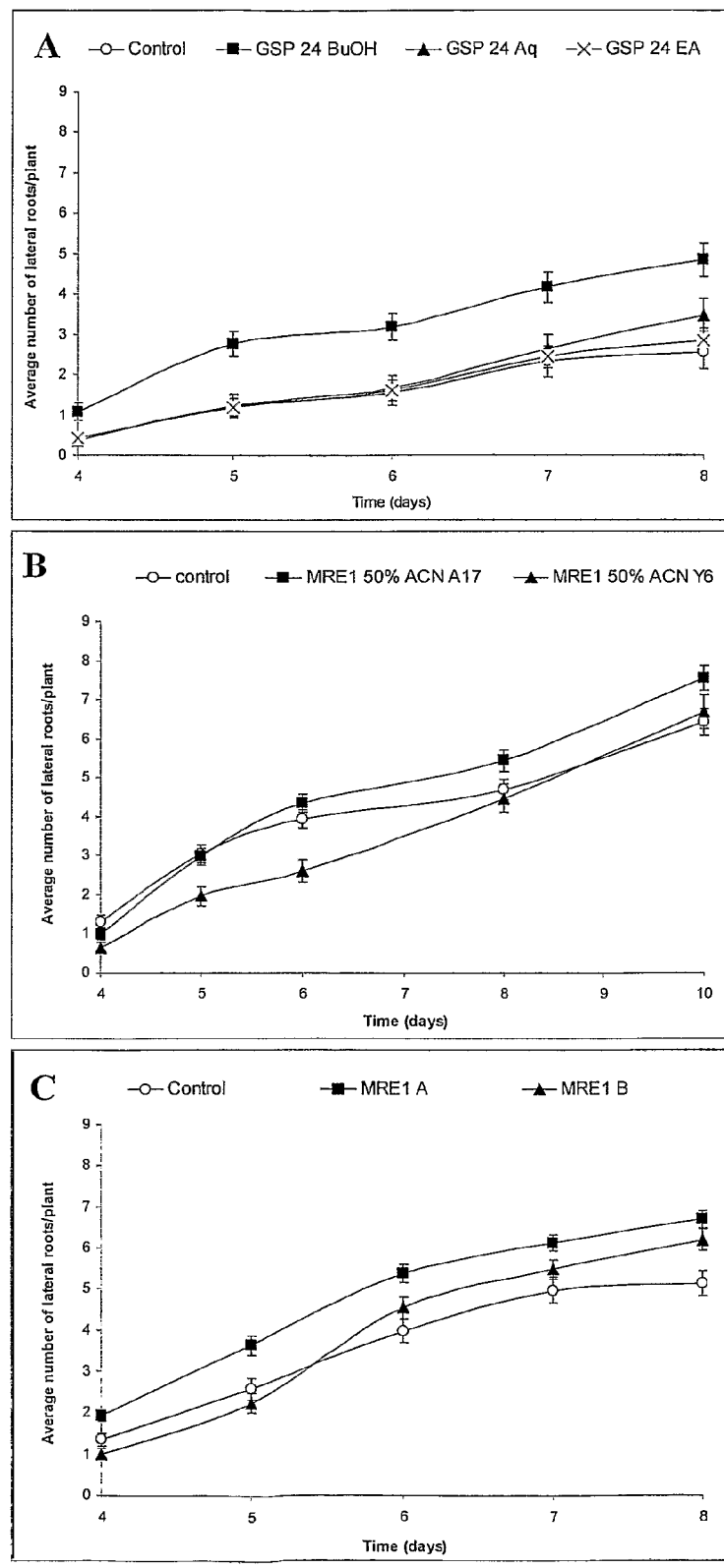

FIG. 10. Effect of Myc Extract Fractions on Lateral Root Formation in *M. truncatula*

(A) The AM fungal signal that stimulates LRF is amphiphilic.

Comparison of the effect of aqueous (Aq), butanol (BuOH) and ethyl acetate (EA) extracts of germinating spore exudates (GSP24) on *M. truncatula* A17. The butanol extract stimulates LRF from day 5 on (significant at P<0.05), whereas the aqueous and acetyl acetate extracts are not active.

(B) LRF stimulation is mediated via the DMI symbiotic signaling pathway.

Comparison of the effect of mycorrhized root exudate (MRE1) butanol extracts, further purified by SPE eluted with 50% acetonitrile, on *M. truncatula* wild-type (A17) and on a dmi1 mutant (Y6). The Myc extract stimulates LRF on the wild-type but not on the dmi1 mutant.

(C) Both fractions A and B stimulate LRF.

Fractions A et B were collected after semi-preparative HPLC of mycorrhized root exudates (MRE-1). Fraction MRE-1 A contained sulfated LCOs and fraction MRE-1 B contained non-sulfated LCOs. Both fractions stimulated LRF significantly (P<0.05).

Figure 11:
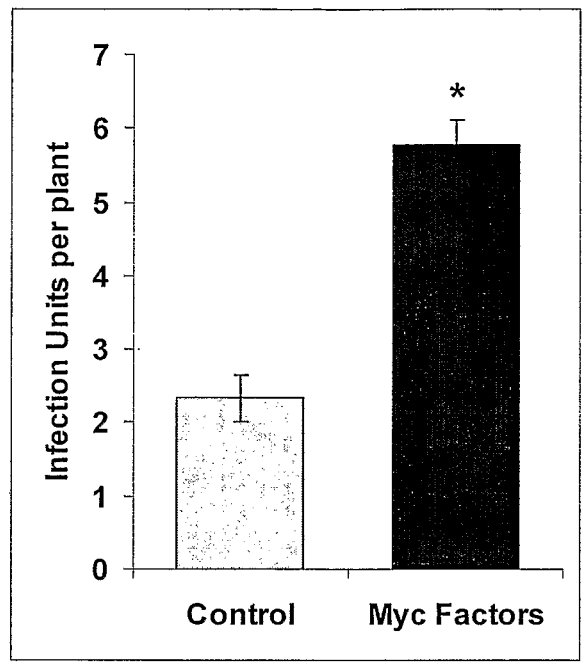
Figure 11:
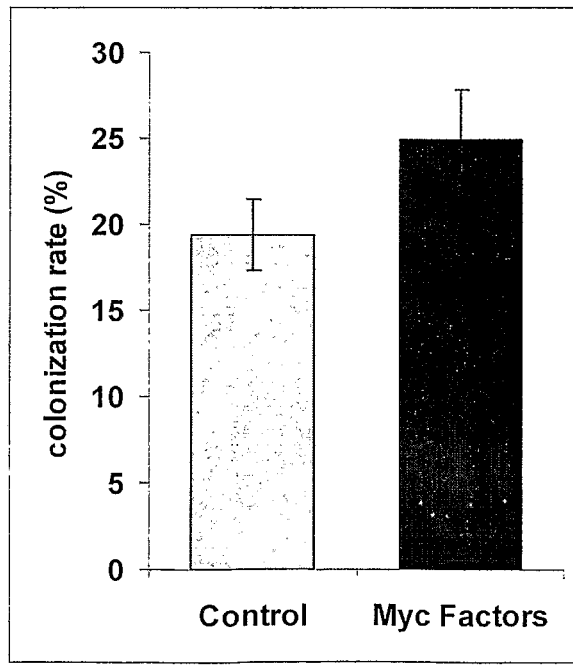

FIG. 11. Effect of a Mixture of Sulfated and Non-Sulfated Myc Factors on Mycorrhization of *Medicago truncatula*.

a. Mycorrhization in axenic conditions. Plants were grown in test tubes on) gellified slopes of M medium in which Myc factors were incorporated at a $10^{-8}$ M concentration. 50 sterile spores (*Glomus intraradices*) were laid close to seedling roots. Extent of mycorrhization was measured by counting the number of infection units six weeks after inoculation. Results were analyzed by the non-parametric Kruskal-Wallis statistical test.

b. Mycorrhization in non-sterile conditions. Plants were grown on a substrate made of charred clay granules, inoculated with 50 sterile spores of *G. intraradices*, Myc factors being added to the nutrient solution at a concentration of $10^{-8}$ M. Three weeks after inoculation root colonization was estimated by the grid intersect method.

Figure 12:
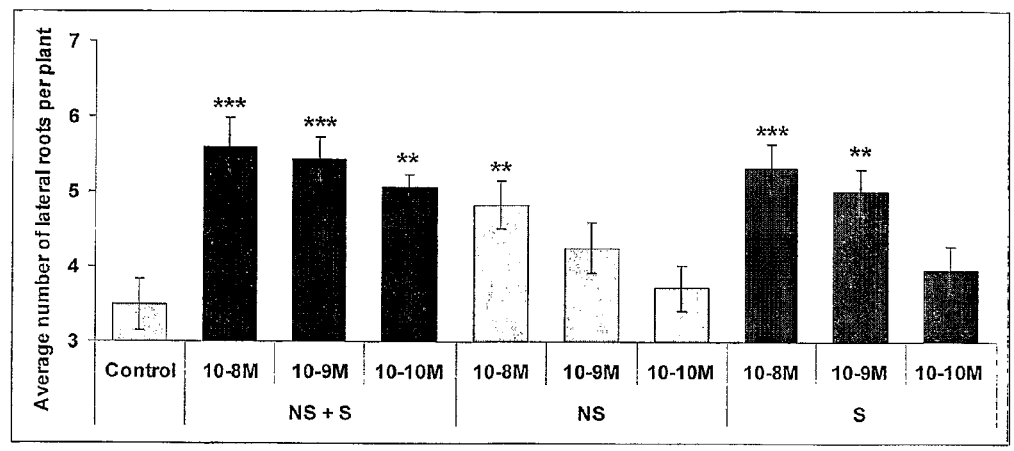
Figure 12:
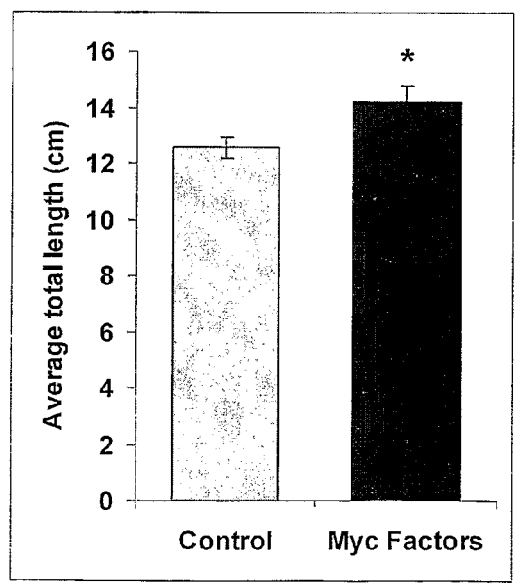

FIG. 12. Effect of Myc Factors on Root Architecture in *Medicago truncatula*.

a. Effect on lateral root formation. Histogram showing the effect of a mixture of both sulfated and non sulfated Myc factors (NS+S), sulfated Myc Factors (S) and non sulfated Myc factors (NS) at $10^{-8}$ M, $10^{-9}$ M and $10^{-10}$ M concentrations on the lateral root formation of *M. truncatula* wild-type (A17), eight days after treatment.

Forty plants were used per experiment and statistical analysis was made by the Student's t-test between control and treated plants.

b. Effect on total root length. Histogram showing the effect of a mixture of sulfated and non-sulfated Myc factors on the total root length of seedlings. Seedling were grown for eight days, roots were cut and the root system was scanned and measured by the WinRhizo software. Data were analyzed by the Kruskal-Wallis test.

(*) and (**) denote respectively a significant (P<0.05) or a highly significant (P<0.01) difference and bars represent the standard error of the mean (SEM).

Figure 13:
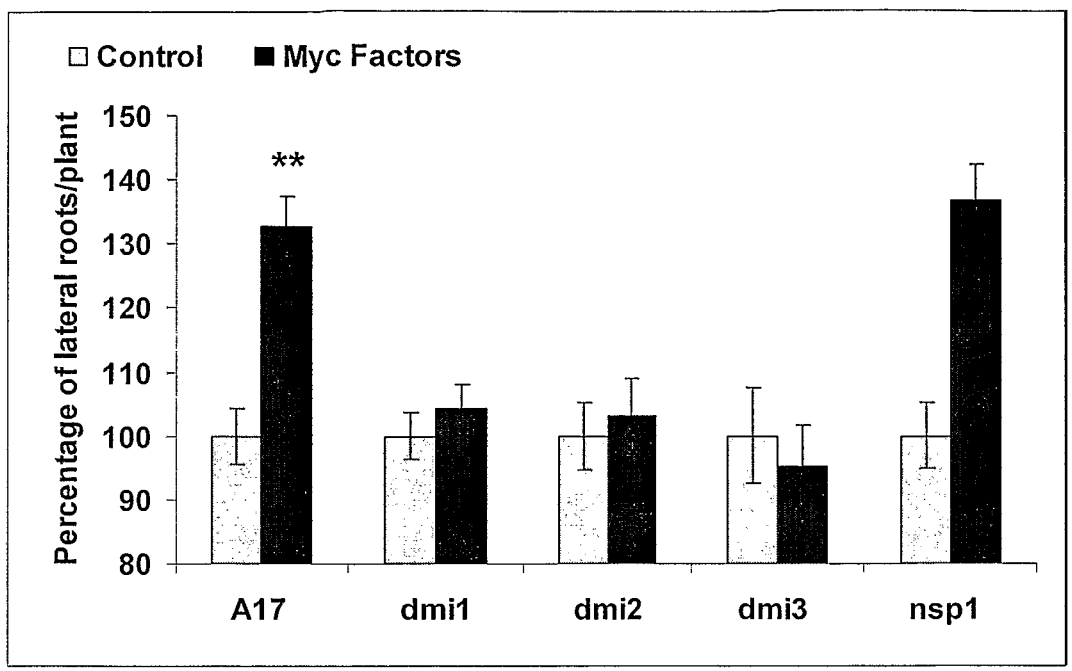

FIG. 13. Genetic Analysis of the Myc Factor-Activated Signalling Pathway Leading to Stimulation of Lateral Root Formation.

Histogram showing the effect of the non-sulfated Myc factor ($10^{-8}$ M) on lateral root formation of *M. truncatula* wild-type (A17) and symbiotic signalling pathway dmi1, dmi2, dmi3 and nsp1 mutants. Means are represented as percentage of the control value eight days after treatment.

For each genotype, data from at least two independent experiments with 40 plants per experiment were pooled and statistical comparisons were made using the Student's t-test between control and each treatment. (**) indicates a highly significant (P<0.01) difference and bars represent the standard error of the mean (SEM).

Figure 14:
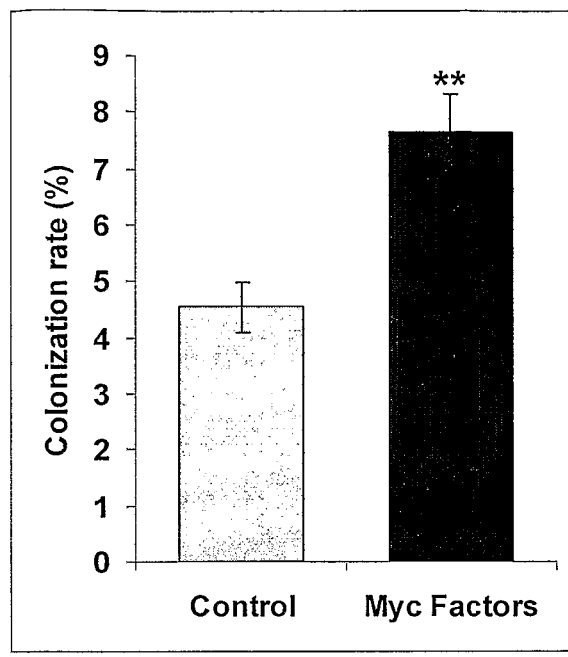
Figure 14:
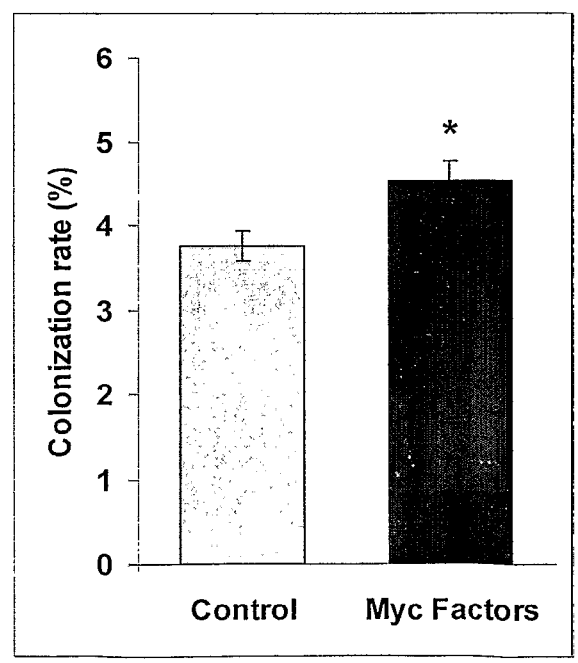

FIG. 14. Effect of Myc Factors on In Vitro Mycorrhizal Colonization of Excised Transformed Roots of Carrot.

a. Effect of a mixture of bacterial sulfated and non-sulfated Myc factors. Roots were inoculated with sterile spores of *G. intraradices* (10 spores/mL of growth medium) and treated once a week during three weeks with or without a mixture of Myc factors at $10^{-8}$ M. The mycorrhizal colonization rate was observed after six weeks. (**) denotes a highly significant difference with control (Student's t test, P-value<0.01). Vertical) bars represent the standard error of the mean (SEM).

b. Effect of a mixture of synthetic sulfated and non-sulfated Myc factors. Roots were inoculated with sterile spores of *G. intraradices* (100 spores/mL of growth medium) and treated once a week during four weeks with or without a mixture of Myc factors at $10^{-8}$ M. The mycorhizal colonization rate was observed after eight weeks. (*) denotes a significant difference with control (Student's t test, P-value=0.0119).

Figure 15:
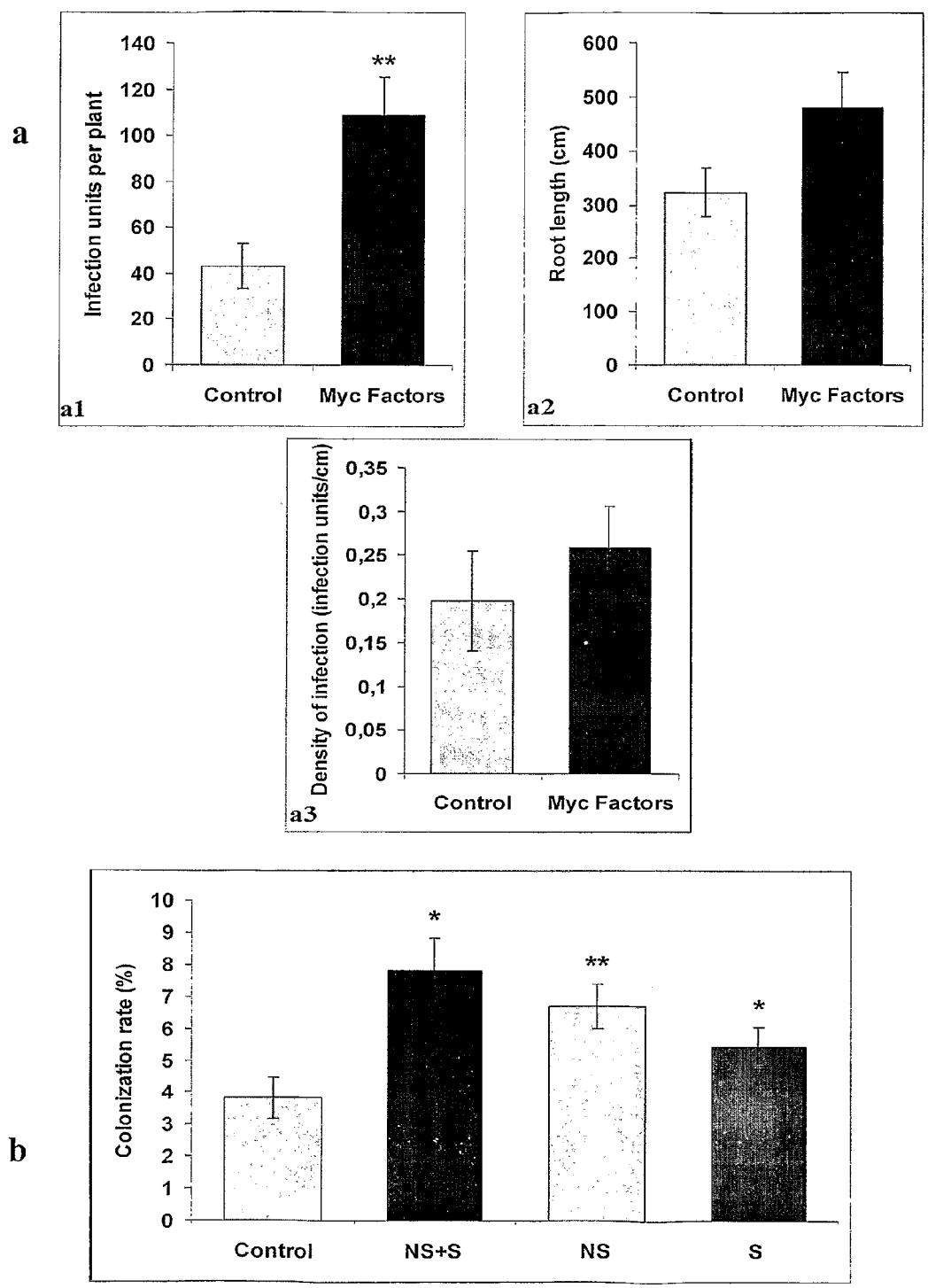

FIG. 15. Effect of Myc Factors on Mycorrhization of *Tagetes patula*.

a: Effect of a mixture of sulfated and non-sulfated Myc Factors on the number of infection units per plant (a1), root length (a2) and density of infection (a3). Plants were inoculated with about 100 sterile spores of *Glomus intraradices* and treated twice a week during three weeks with or without Myc factors at $10^{-8}$ M. The number of infection units, root length and the density of infection units were determined after four weeks. (**) denotes a highly significant difference with control (Student's t test, P-value=0.004086).

b: Effect of sulfated (S), non-sulfated (NS) or a mixture of both sulfated and non-sulfated (NS+S) Myc Factors on the mycorrhizal root colonization. Plants were inoculated with about 100 sterile spores of *G. intraradices* and treated twice a week during three weeks with or without Myc factors at $10^{-8}$ M. The colonization rate was measured after four weeks.

Figure 16:
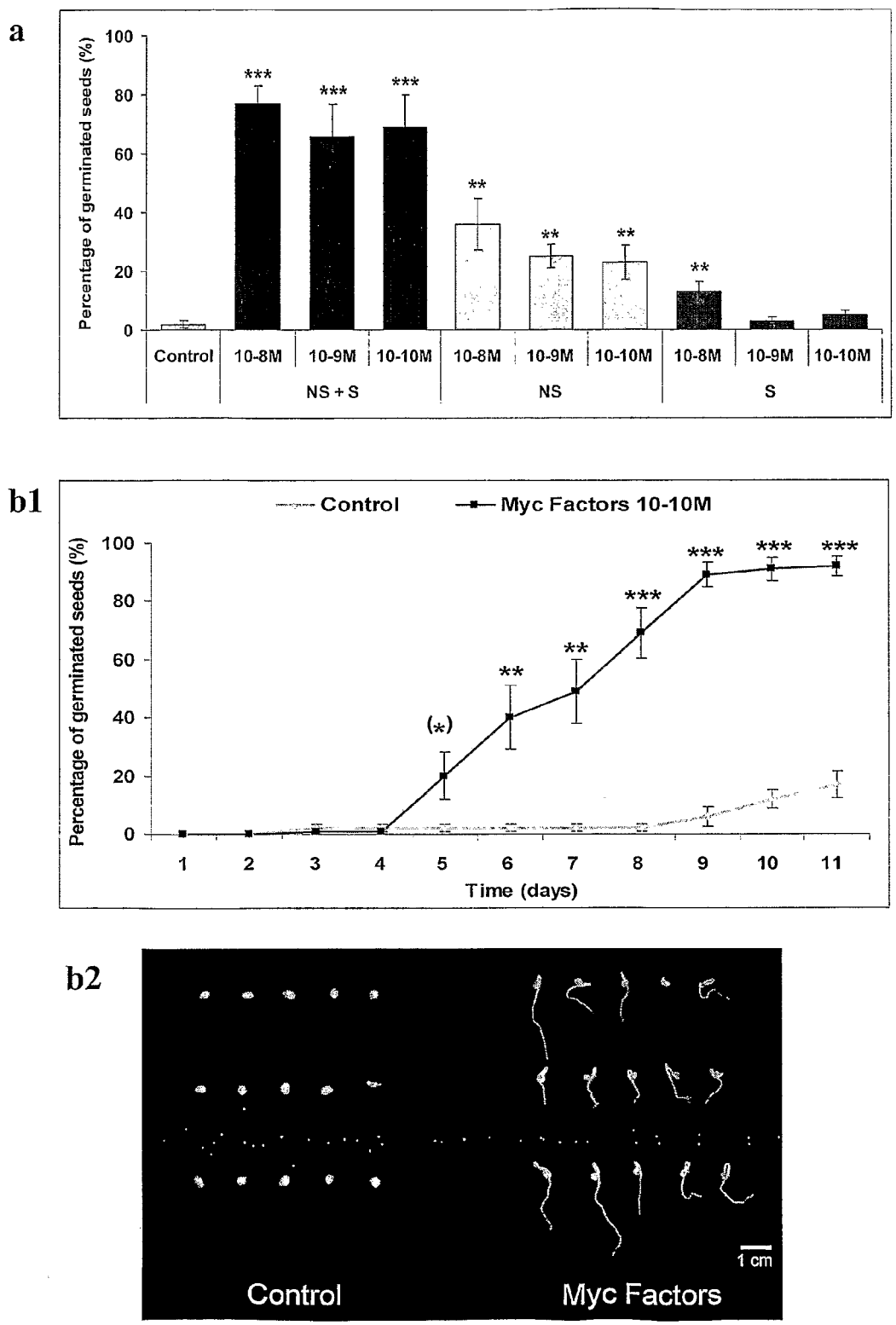

FIG. 16. Effect of Myc Factors on Germination of Tomato Seeds.

a. Effect of non-sulfated (NS), sulfated (S), and a mixture of both sulfated and non-sulfated (NS+S) Myc Factors on germination of tomato seeds at 14° C. Myc factors were added to germination plates at $10^{-8}$ M, $10^{-9}$ M and $10^{-10}$ M. Germination rate was scored everyday. Results were analyzed with the Kruskal-Wallis test. (*) and () denotes respectively a very highly (P-value<0.001) and highly (<0.01) significant difference with control, and vertical bars represent the standard error of the mean (SEM).

b. Effect of a mixture of sulfated and non-sulfated Myc factors on seed germination at 14° C.

b1. Kinetics of germination. Myc factors were added at $10^{-10}$ M. Results were analyzed with the non-parametric Kruskal-Wallis test. After day 6, differences were highly significant. Vertical bars represent the standard error of the mean (SEM).

b2. Photograph of representative germination plates with and without Myc factors ten days after sowing.

MATERIALS AND METHODS

Natural Sources of Myc Factors

The AM fungus *Glomus intraradices* strain DAOM 197198, which has been maintained in co-culture with excised roots for many years (Chabot et al., 1992), is well characterized and its genome is being sequenced. This strain is used by PREMIER TECH company for the industrial preparation of commercial inoculants and for the production of purified spores for research purpose. For example, these purified spores were used as a source of DNA for the project of *G. intraradices* genome sequencing. We used two sorts of exudates, both prepared from materials purchased from PREMIER TECH BIOTECHNOLOGIES (Rivère-du-Loup, Québec, Canada):

(i) Exudates from mycorrhized roots (EMR). Mycorrhiza production was achieved by co-cultivation of *G. intraradices* with excised transformed roots of carrot. The growth medium was solidified with Phytagel. After appropriate growth of the mycorrhized roots, the gel was liquefied by adding sodium citrate as chelating agent, and the liquid EMR was conditioned in 4 liter containers which were stored at 4° C.

(ii) Exudates from germinating spores (GSP). Purified sterile spores of the AM fungus *Glomus intraradices* were conditioned by bottles containing approximately one million of spores. Bottles were stored at 4° C. Spores were germinated at 30° C. in a 2% $CO_2$ incubator for 10 days.

Bioassays Used for Purification of Myc Factors

To detect the presence of AM fungal symbiotic signals during the various steps of extraction and purification, three bioassays were used. (i) The *M. truncatula* ENOD11::GUS construct was shown to be induced during mycorrhiza formation and by a diffusible compound from diverse AM fungi (Journet et al., 2001; Kosuta et al. 2003) (=MtENOD11 assay). (ii) The lateral root formation in *M. truncatula* was shown to be stimulated by a diffusible compound from diverse AM fungi and the response required the DMI symbiotic signaling pathway (Olah et al., 2005) (=MtLRF assay). (iii) In addition we used a modified *Vicia sativa* (vetch) root hair branching assay which allows the detection of various non-sulfated LCOs (=VsHab assay).

(i) Induction of the Symbiotic MtENOD11 Gene in Transgenic *Medicago truncatula*.

We have previously shown by experiments in which the AM fungus was separated from the plant root by a cellophane membrane that a diffusible AM fungal compound can induce the expression of an MtENOD11 promoter-gusA transgene in growing lateral roots of *M. truncatula* (Kosuta et al., 2003). The protocol used was as previously described (Andriakaja et al., 2007) with the following modifications: no paper disc was inserted on the top of the agar plate and the treatment was made by addition of 40 microliters per seedling. To check whether the ENOD11 response was induced via the DMI signaling pathway, we compared the response observed in the *M. truncatula* wild-type line A17 and in a mutant line carrying a mutation in the DMI1 gene (Y6 mutation).

(ii) Root Hair Branching of Vetch

Vetch (*Vicia sativa* subsp. *nigra*) is a small seeded legume which is convenient for the microscopical observation of root hair deformations. Vetch root hair) deformations are elicited not only by the Nod factors of the specific bacterial symbiont *Rhizobium leguminosarum* by. *viciae* but also by a variety of non-sulfated Nod factors (Roche et al., 1991; Price et al., 1992).

This assay is thus appropriate to detect the presence of non-sulfated LCOs. In previous reports the assay was done in a liquid medium. We have devised an assay on agar plate which is more sensitive and reproducible. Seeds were first sterilized in sulfuric acid for 20 min, rinsed twice with sterile water, and then treated for 20 min in calcium hypochlorite (5 g/150 ml after paper filtration) and rinsed five times with sterile water. Seeds were left in water overnight at 4° C., transferred onto soft agar plates and incubated three days at 4° C. to increase the homogeneity of germination. Plates were then left for 36 hours at 22° C. in the dark for germination. Five young seedlings (root length of approximately 1 cm) were sown in Petri dish, on Fahraeus agar plates, surrounded with parafilm, and left three days, in a vertical position in a growth chamber at 22° C. When roots became hairy, 40 microliters of the solution to be tested were gently deposited along the roots, and seedlings were grown for 30 hours at 22° C. For root hair branching observation, roots were sectioned, inserted between a slide and a cover-slip in a 0.02% methylene blue solution, and observed under a light microscope. Ten plants were observed per treatment.

Mycorrhization Assays

Sources of AM fungal inoculum for mycorrhization experiments were sterile spores of *Glomus intraradices*, either purchased from Premier Tech Biotechnologies Ltée (Rivière-du-loup, Québec, Canada) or produced on excised transformed carrot roots as described by Bécard and Fortin (1988). Mycorrhized transformed carrot roots were grown as described in Chabot et al. (1992) and subcultured every ten weeks on M medium (Bécard and Fortin, 1988) gellified with 0.4% Phytagel (Sigma). After solubilization of Phytagel with citrate buffer (Doner and Bécard, 1991), spores were collected as described under sterile conditions and stored at 4° C. in Ultrapure water for at least four weeks before use.

Mycorrhization tests were carried out on three plant species, the model legume *M. truncatula* and two non-legumes, carrot (*Daucus carota*, Umbelliferae family) and French marigold (*Tagetes patula*, Asteraceae family).

Myc factors were dissolved in water/acetonitrile (50/50) to prepare a $10^{-3}$ M stock solution, which was then diluted to the appropriate concentration with water or growth medium. The same amount of acetonitrile solvent traces was added to control plates.

In Vitro Mycorrhization of Excised Transformed Carrot Roots

Sterile excised transformed carrot roots were grown on M medium solidified by 0.4% phytagel, at 24° C. in the dark, and subcultured every ten weeks (Chabot et al., 1992). Roots were collected by solubilization of Phytagel with citrate buffer (Doner and Bécard, 1991) and washed with sterile deionised water. Plates for mycorhization assay were prepared as follows: in Petri dishes (Ø 90 mm) a first layer of 20 ml M medium containing 0.3% Phytagel was poured and left for solidifying. A second layer of the same medium was then poured containing 20 or 200 spores/ml and Myc factors at the appropriate concentration. In control plates Myc factor solution was replaced by the same volume of the medium used for preparing the Myc factor solution. Root fragments were laid on the medium surface with approximately the same amount (number of fragments and root length) in the different plates. Dishes were closed with Parafilm tape and incubated in the dark, in a growth room at 24° C. and 50% humidity, during six or eight weeks. Myc factors were added once a week on the plate surface during the three or four first weeks for experiments of six or eight weeks respectively. To observe fungal colonization, roots were collected after liquefaction of phytagel by citrate buffer, washed and stained by the ink-vinegar method (Vierheilig et al., 1988). Colonization rate was estimated by the grid intersect method (Giovanetti and Mosse, 1980).

In Vivo Mycorrhization of *Tagetes patula*

Seeds of *Tagetes patula*, var. Légion d'honneur, were obtained from Caillard (84091 Avignon, France). Seedlings were grown four weeks in 50 ml Falcon tubes filled with a substrate made of washed and autoclaved clay (charred granular Montmorillonite; ref "Oil Dry US Special", Brenntag Bretagne, ZI de Tory, BP41, Avenue des Ferrancins, 71210 Montchanin). To ensure watering of the seedlings, tubes were pierced with three small holes at the bottom, and individually placed in 120 ml plastic boxes (5.5 cm diameter/7 cm high), closed with an opaque cap pierced to receive and fix the Falcon tubes.

Boxes were filled with 80 ml water and wrapped with aluminium foil. The Falcon tubes clay substrate was hydrated with 20 ml Long Ashton low phosphate solution (Hewitt et al, 1966). In each tube one seed was placed underneath the surface of the substrate, and a hundred of fungal spores were dropped around the seed, in 1 ml $10^{-7}$ M Myc factor or control solution. Each plant received 1 ml $10^{-7}$ M Myc factor, or 1 ml control solution, twice a week for three weeks. Pots were placed in a growth chamber, at 25° C., with a 16 h photoperiod and a light intensity of 180 µEinstein.$m^{-2}.s^{-1}$.

Two series of experiments were done. In the first, a mixture of sulfated and non-sulfated synthetic Myc Factors was tested with 12 seedlings per treatment. In the second, sulfated, non-sulfated and a mixture of both were tested with 20 seedlings per treatment. Plants were harvested after 4 weeks. The inner root system was stained with Schaeffer black ink (Vierheilig et al, 1998). Quantification of root colonization by the fungus was performed under a binocular magnifying glass, and two methods were used: (i) for the first experiment, the number of infection units (zones containing arbuscules, vesicles and internal hyphal networks) was counted for each plant, and (ii) for the second, the percentage of root length colonized by the fungus, that is, showing arbuscules, vesicles or both, was determined by the) gridline intersect method (Giovannetti et al, 1980).

Mycorrhization of *Medicago truncatula* in Axenic Conditions

Plants were grown in test tubes on slopes of 20 ml gellified MM medium (Olàh et al, 2005) as described in Ben Amor et al. (2003). Myc factors at $10^{-8}$ M concentration (or control solution) were incorporated directly into the sterile medium. Fifty sterile spores of *G. intraradices* were put at the bottom of each slope near the seedling root. Test tubes were placed in a growth chamber at 25° C. with a 16 h photoperiod and light intensity of 366 µEinstein.m$^{-2}$.s$^{-1}$. After six weeks, the root system architecture was analysed by the Winrhizo Scientific Software (Instruments Regent Inc, 2672 Chemin Ste Foy RD, Sainte Foy, Quebec, Canada). Quantification of root colonization was done by direct counting of infection units under a binocular glass magnifier, after root staining by the ink-vinegar method (Vierheilig et al, 1998).

Mycorrhization of *Medicago truncatula* on a Charred Clay Substrate

Germinated seedlings were grown for three weeks in 50 ml Falcon tubes as described above for *Tagetes* mycorrhization. Twenty *G. intraradices* spores were dropped around the seedling roots, in 1 ml of $10^{-7}$ M Myc factor or control solution. Then each plant received 1 ml of $10^{-7}$ M Myc factor, or 1 ml control solution, twice a week during two weeks. Two series of experiments were done with 12 seedlings per treatment. Pots were placed in a growth chamber, at 25° C., with a 16 h photoperiod, and light intensity of 366 µEinstein.m$^{-2}$.s$^{-1}$.

Plants were harvested after 3 weeks. The inner root system was stained with Schaeffer black ink (Vierheilig et al, 1998). The percentage of root length colonized by the fungus, that is, showing arbuscules, vesicles or both, was determined by the gridline intersect method (Giovannetti et al, 1980)

Bioassays Used for Testing the Developmental Activity of Myc Factors

Bioassays were devised to study the developmental activity of purified or synthetic Myc factors.

(i) Stimulation of Root System Development in the Model Legume *M. truncatula*.

We have previously shown that a diffusible factor from AM fungi stimulates the lateral root formation (LRF) in *M. truncatula* via the DMI pathway (Olah et al., 2005). We have used this bioassay to test the developmental activity of purified Myc factors. The protocol used was as described previously except that vitamins were not added to the M medium.

Identification of plant genes involved in Myc factor signaling was performed in *M. truncatula*, using the genetic analysis of the LRF response already described (Olah et al., 2005). LRF responses to Myc factors were studied in the wild-type *M. truncatula* Jemalong A17 line, as a control, and in the symbiosis-defective mutants dmi1 (Y6), dmi2 (TR25), dmi3 (TRV25), and nsp1 (B85).

(ii) Tomato Seed Germination

Seeds of tomato variety Heinz 1706 were from the Core collection of tomato seeds of INRA. They were kindly provided by Rene Damidaux of the "Génétique et Amélioration des Fruits et Légumes" laboratory at INRA 84143 Montfavet cedex (France). From this core collection sample, seeds were multiplied at LIPM (INRA-CNRS, Toulouse). Seeds were stored at 4° C. Seeds were sterilized for 45 min in a filtered solution of 0.262 M calcium hypochlorite (2.5 g of CaOCl2 in 75 ml water), to which two drops of Tween 20 had been added. Hypochlorite solution was removed and seeds were rinsed three times with sterile distilled water. Germination agar plates were prepared by dissolving 9.375 g of Difco Agar Granulated (Becton-Dickinson) in one liter of distilled water. A solution of $10^{-3}$ M Myc factor was prepared in 50/50 water/acetonitrile, and was then diluted to the appropriate dilutions with water. The same amount of acetonitrile solvent traces was added to the control plates. Fifteen seeds were laid by plate, with six or eight repeats per treatment. Plates were incubated in the dark at 14° C., 20° C. and 28° C. Germination rate was scored everyday.

Statistical Analysis of Data.

Data of biological assays were statistically analyzed with the Student's t-test or analysis of variance for data following a normal distribution and having homogeneous variances, and Kruskal-Wallis or Wilcoxon non-parametric tests for non-normal distributions. Statistical software was from the R system (R Development Core Team, 2009).

Biochemical Analyses

Liquid/Liquid Extraction for Mycorrhized Roots Exudates:

In a two liter bulb, 1.6 liter of mycorrhized root exudates was extracted a first time with 400 ml (¼ of volume) butanol (1-butanol or 2-methyl-1-propanol) and the mixture was left for decantation to get a clear butanol phase with a thin interphase, permitting a good separation of the aqueous and butanol phases (at least six hours). The aqueous phase was then extracted a second time with 350 ml (approximately ⅕ of volume) butanol and left overnight. After this second extraction, the total butanol phase (extraction 1 and extraction 2) was evaporated to a volume of approximately 0.5 liter, which was washed by a liquid/liquid extraction with the same volume of bi-distilled water. The washed butanol phase was evaporated, transferred in a small balloon and dried using a rotary evaporator. The dry extract was then re-dissolved in 5 ml water/acetonitrile (1/1) and filtered on cotton (preliminary washed with chloroform) in a 8 ml glass tube and then dried under nitrogen flux.

Liquid/Liquid Extraction for Germinating Spores Exudates:

Exudates from one million of germinating spores (approximately 150 ml) were first extracted with ⅓ of volume of ethyl acetate. The mixture was left for decantation to get a thin interphase and a good separation of the aqueous and ethyl acetate phases (at least six hours). The aqueous phase was extracted a second time with ⅓ of volume of ethyl acetate overnight. The aqueous phase was then extracted with butanol (1-butanol or 2-methyl-1-propanol) following the same steps as for the ethyl acetate extraction. The butanol and ethyl acetate phases volumes were reduced to few ml using a rotary evaporator. Each phase was transferred into a 5 ml tube and dried under nitrogen flux.

Purification by Solid Phase Extraction (SPE):

Column preparation: The SPE system was made up of a Chromabond 3 ml glass column filled with C18 reverse phase (SUPELCO Discovery DSC-18). A first glass fiber filter was introduced at the bottom of the column. The solid phase was added into the column to represent 3.5 cm height in the column. A second glass fiber filter was laid on top of the solid phase and pushed in to compress the solid phase. Before use, the column was washed with acetonitrile (ACN) and with water, and then conditioned with acetonitrile (ACN) 20% in water.

Pre-filtration: Extract was dissolved in one ml of 20% ACN. The extract was filtered on cotton in a Pasteur pipette (preliminary washed with chloroform) and deposited on the C18 column. The tube and the filters were rinsed with 1.5 ml of ACN 20%.

Chromatography: Using a syringe, the extract was pushed through the C18 phase. The running out liquid of the column was collected in an 8 ml glass tube. To get rid of the non-adsorbed compounds, the phase was abundantly washed (equivalent 5 times the volume of the solid phase with 20% ACN in water). This volume was recovered in the same tube. Then molecules retained on the column were eluted with a 50% solution of ACN in water. The elution volume being equivalent to 5 times the solid phase volume was recovered in a second glass tube. Finally the strongly adsorbed molecules were eluted from the column with 100% ACN. The volume of solvent (about 6 ml) was recovered in a third tube. The three solutions (20%, 50% and 100% of ACN) were evaporated under nitrogen flux, in order to get dry residues. Each residue could then be re-dissolved in the volume appropriate to realize the semi-preparative HPLC. A SPE column was used to purify approximately 5 liters of mycorrhized root exudates.

Semi-Preparative HPLC:

Purification was performed on a High-Performance Liquid Chromatography Shimadzu LC10 separation module (Shimadzu corporation, Kyoto, Japan) with a semi-preparative C18 reverse phase column (8 mm×250 mm; 5 μm, Equisorb, CIL-Cluzeau). The injection loop had 100 microliter volume. The chromatographic procedure was the following: for 10 min in isocratic mode with solvent A (20% acetonitrile in water), followed by a linear gradient for 20 min from solvent A to solvent B (100% acetonitrile) and another isocratic step at 100% acetonitrile for 5 min. Two minutes are necessary to come back to the initial conditions (20% ACN). The flow rate was 2 ml min$^{-1}$ and UV absorption was monitored at 206 nm. Collection of samples along the gradient was done every minute (2 ml) resulting in 14 fractions.

Supplementary Analytical HPLC for Detection of Non-Sulfated LCOs

Purification was performed on a High-Performance Liquid Chromatography Shimadzu LC10 separation module (Shimadzu corporation, Kyoto, Japan) with a C8 phase column (Zorbax XDB-C8 HP-Eclipse (Hewlett Packard) 5 μm, 4.6×150 mm) for 5 min in isocratic mode with 30% methanol in water solvent, followed by a linear gradient for 20 min to the 100% methanol solvent, followed by another isocratic step at 100% methanol for 5 min. 2 min were necessary to come back to the initial conditions. The flow rate was of 1 ml min$^{-1}$ and the UV absorption was monitored at 206 nm. Collection of samples occurred along the gradient and isocratic step at 100% methanol every minute (about 1 ml) from 15 to 23 min producing 8 fractions.

UPLC-ToF MS Analyses:

Each fraction collected from semi-preparative HPLC was submitted to UPLC-MS analysis on an Acquity UPLC coupled to Q-Tof Premier mass spectrometer (Waters Corporation). The UPLC column was an Acquity column (2.1 mm×10 cm, 1.7 μm) (Waters, USA), and the flow rate was 0.45 ml/min. For the more hydrophilic compounds (semi-preparative HPLC fractions 1 to 9) the program was a linear gradient ranging from 10% ACN (in 1% acetic acid/water) to 100% ACN within 7 minutes, followed by an isocratic step at 100% ACN for 2 min and then a return to the initial conditions (2 min) and finally a reconditioning step of 1 min with 10% ACN (in 1% acetic acid/water). To get a better resolution of the more hydrophobic compounds (semi-preparative HPLC fractions 6 to 11) the UPLC gradient was more extended: linear gradient starting at 25% ACN in 0.1% acetic acid/water and reaching 100% ACN within 7 minutes. For the mass spectrometer, capillary was set to 3.2 kV and the cone to 10 V. Internal lock mass was performed by continuous introduction into the source of a Leucine-enkephalin solution. Spectrometer was calibrated before each experiment. The more hydrophilic compounds (semi-preparative HPLC fractions 1 to 9) were analyzed in both the negative and positive modes in order to facilitate respectively the detection of anionic (sulfated) and cationic (non-sulfated) compounds.

For fragmentation of molecules, specific ions were selected and submitted to MS/MS analysis using collision energy at 15V.

Mild Hydrolysis:

This method is used to remove the sulfate moiety of sulfated LCOs without affecting the rest of the molecules (Roche et al., 1991b). Fraction A, eluting between 15 and 16 min on semi-preparative HPLC, was transferred in a screw glass vial and dried under nitrogen flux. It was re-dissolved two times in anhydrous methanol and dried again, in order to remove residual water. 250 μl of 0.05M HCl in methanol was added to the dry sample. The reaction was carried out overnight at room temperature. The sample was then dried again under nitrogen flux and washed twice with anhydrous methanol, in order to remove all the acid.

Production of Milligram Quantities of Myc Factors

Purification of Myc factors from exudates of germinating spores of *Glomus intraradices* and of mycorrhized roots results in extremely low yields. Two strategies have been used to produce large amounts of these molecules, making use of bacterial genetic engineering.

(i) Production of Myc Factors by *Rhizobium* Mutants.

Rhizobia produce Nod factors that are substituted LCOs that share some structural similarities with Myc factors. The major difference is that Myc factors are very simple LCOs with a very limited number of substitutions, essentially restricted to the possible O-sulfation of the reducing N-acetyl glucosamine residue. Our strategy was to use rhizobial mutants altered in genes coding for enzymes responsible for substitutions of Nod factor precursors and therefore secreting very simple LCOs similar to Myc factors. We chose to use mutant strains derived from rhizobial species which produce a majority of tetrameric LCOs and a minority (about 10%) of pentameric LCOs, as in the case of fungal Myc factors.

For the production of sulfated Myc factors we used a *Sinorhizobium meliloti* nodFEnodL double mutant. The nodL mutation suppresses O-acetylation of the non-reducing Gluc-NAc terminal residue, and the nodFE mutation blocks the synthesis of the unsaturated 16:2 fatty acid resulting in the N-acylation with C18:1 (vaccenic) or C16:0 (palmitic) fatty acids (Ardourel et al., 1994). To increase the production of LCOs, a multicopy plasmid carrying regulatory nod genes (pMH682) was introduced in the mutant strain. The resulting overproducing strain, GMI 6629, was grown in a liquid growth medium containing 5 µg/ml tetracycline to maintain the presence of the pMH682 plasmid and luteolin (10 µM) as a nod gene inducer (Ardourel et al, 1994). When the bacterial culture reached a cell density of about $10^9$ cells per ml, Nod factors were extracted by liquid/liquid extraction with butanol and ethyl acetate (Roche et al, 1991). LCOs were then purified by HPLC on a C18 reversed-phase column as previously described (Lemont et al, 1993), with the following water-acetonitrile) gradient modification: a 10 min isocratic phase at 20% acetonitrile was followed by a linear gradient running from 20 to 65% acetonitrile for 30 min at a flow rate of 2 ml/min. The peaks containing sulfated LCOs were collected between 32 and 35% acetonitrile, and analyzed by mass-spectrometry. A majority of LCOs was tetrameric and a minority pentameric, as for Myc factors. LCOs were O-sulfated at the reducing end and N-acylated with C18:1 and C16:0 fatty acids at the non-reducing end. No O-acetyl substitutions could be detected.

For the production of non-sulfated Myc factors the strain LPR5045 (pMP247) was used. It is a derivative of the *R. leguminosarum* bv. *trifolii* strain RCR5, cured from the Sym plasmid, in which a multicopy plasmid containing the common nodABCIJ genes (=pMP247) was introduced (Lugtenberg et al, 1995). This overproducing strain was grown in B-culture medium with 5 µg/ml tetracycline for maintaining the pMP247 plasmid and 10 µM naringenin as a nod-gene inducer (Spaink et al, 1994). LCOs were extracted from the culture medium as described above. HPLC purification was performed with the same C18 reversed-phase column as for sulfated LCOs, with a 20 min isocratic phase at 26.5% acetonitrile followed by a linear acetonitrile-water gradient from 26.5% to 100% acetonitrile for 40 min at a flow rate of 2 ml/min. Peaks corresponding to non-sulfated LCOs were collected at about 50% acetonitrile and analyzed by mass spectrometry. A majority of LCOs was tetrameric and a minority pentameric, as for Myc factors. N-acylation was with C18:1 and C16:0 fatty acids. No O-acetyl or O-sulfate substitutions could be detected.

The structure of the major sulfated and non-sulfated LCOs produced by the rhizobial mutant strains, *Sinorhizobium meliloti* GMI 6629 and *Rhizobium leguminosarum* bv. *trifolii* LPR5045 (pMP247), respectively is represented below. They are perfect mimes of the Myc factors produced by the AM fungus *Glomus intraradices* (see Example 2).

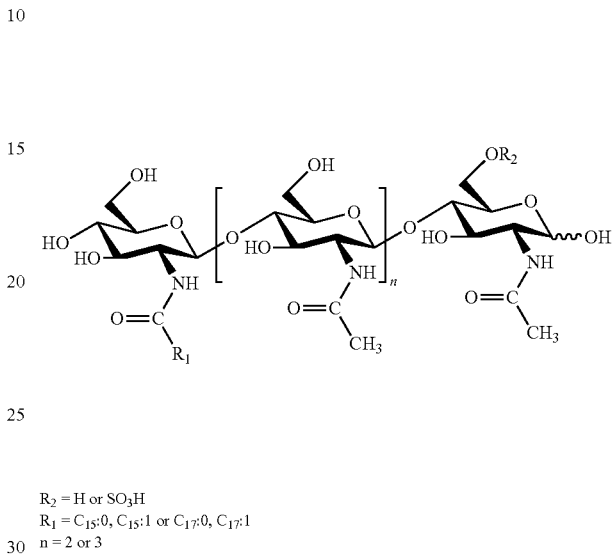

$R_2$ = H or $SO_3H$
$R_1$ = $C_{15}:0$, $C_{15}:1$ or $C_{17}:0$, $C_{17}:1$
n = 2 or 3

These Myc factors, prepared from rhizobial mutant cultures, were tested for biological activity. Example 7 shows that a mixture of these sulfated and non-sulfated Myc factors greatly stimulates mycorrhiza formation (FIG. 14A), demonstrating that these molecules act as genuine mycorrhizal signals.

(ii) Production of Myc Factors by the Cell Factory Approach.

These synthetic Myc factors were kindly provided by Eduardo Andres Martinez and Hugues Driguez of CERMAV CNRS laboratory in Grenoble, France. The procedure that they used was essentially as described in the literature (Samain et a, 1999): high cell density cultivation of recombinant *E. coli* strains harboring the nodBC or nodBCH genes from *Sinorhizobium meliloti* afforded $N^{I,II,III}$-triacetyl-chitintetraose and $6O^I$-sulfated-$N^{I,II,III}$-triacetyl-chitintetraose as major compounds together with small amounts of their corresponding pentamers.

After extraction and purification of these compounds, selective N-acylation was conducted using hexadecanoic or oleic acid chlorides in various hydro-organic solvents or by using the free acids, and the N-acylation procedure previously developed for the preparation of lipochito-oligosaccharide nodulation factors (Ohsten Rasmussen et al, 2004).

The following four lipochitosaccharides were prepared:
LCO IV (contaminated with ≈ 10% of LCO V) C16:0
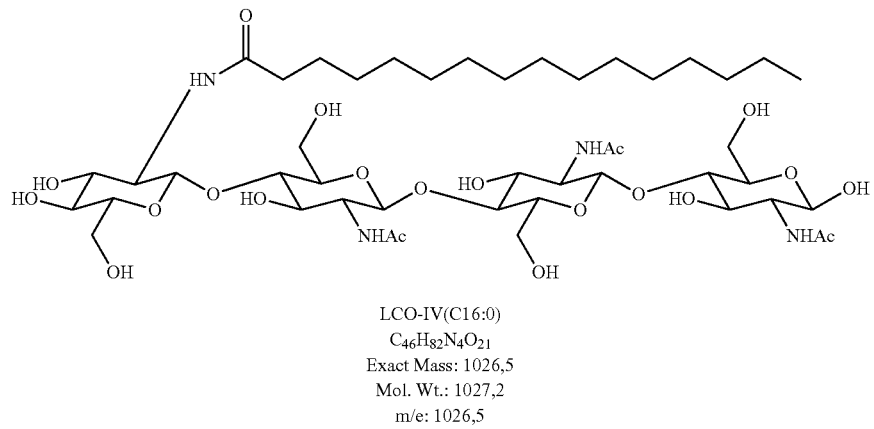
LCO-IV(C16:0)
$C_{46}H_{82}N_4O_{21}$
Exact Mass: 1026,5
Mol. Wt.: 1027,2
m/e: 1026,5
LCO IV (contaminated with ≈ 10% of LCO V) S C16:0
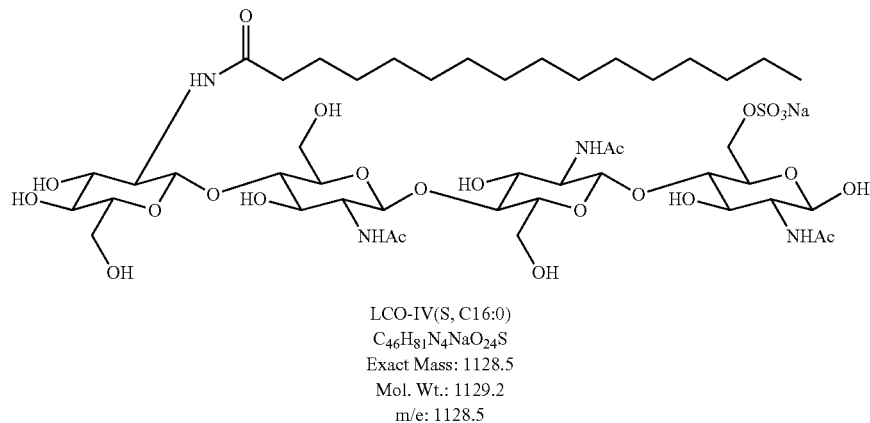
LCO-IV(S, C16:0)
$C_{46}H_{81}N_4NaO_{24}S$
Exact Mass: 1128.5
Mol. Wt.: 1129.2
m/e: 1128.5
LCO IV (contaminated with ≈ 10% of LCO V) C18:1
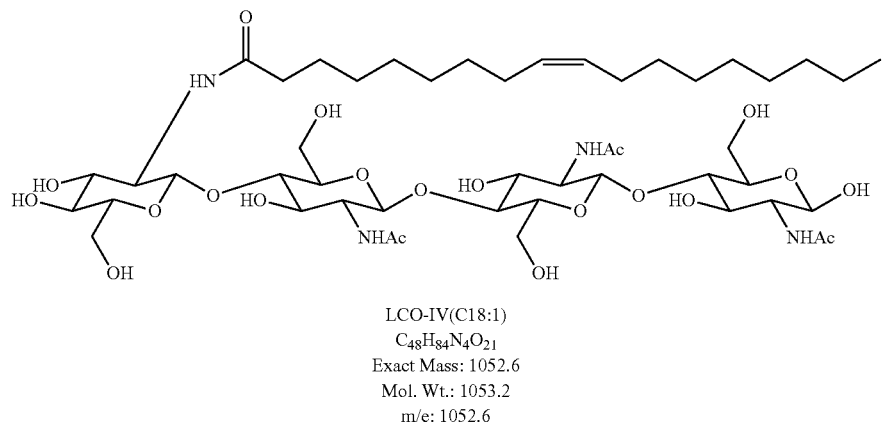
LCO-IV(C18:1)
$C_{48}H_{84}N_4O_{21}$
Exact Mass: 1052.6
Mol. Wt.: 1053.2
m/e: 1052.6

LCO IV (contaminated with ≈ 10% of LCO V) S C18:1

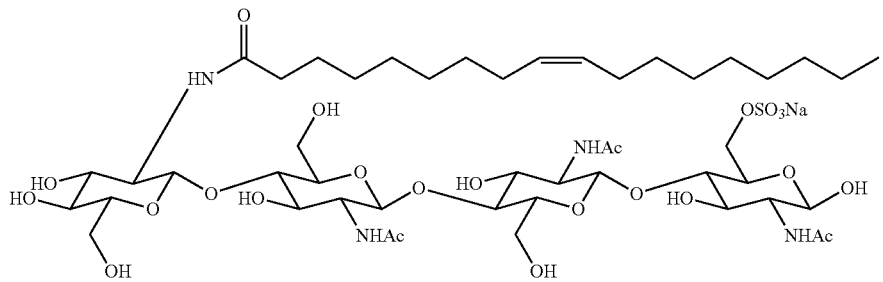

LCO-IV(S, C18:1)
$C_{48}H_{83}N_4NaO_{24}S$
Exact Mass: 1154.5
Mol. Wt.: 1155.2
m/e: 1154.5

Results

EXAMPLE 1

Purification of MYC Factors from Mycorrhized Roots Exudates and from Germinating Spores Exudates General Strategy

*Glomus intraradices* strain DAOM 197198 was used as a source of Myc factors because this strain has a broad host-range and is used for large-scale industrial production of AM fungi inoculants. This strain is well characterized and its genome is being sequenced. Two sources of Myc factors were used in a complementary manner. Exudates from mycorrhized roots have the advantage of permitting extraction from large volumes with the possibility of obtaining significant amounts of Myc factors. The disadvantage of this source is that exudates contain a mixture of compounds from both plant and fungal origin. This is why we also used another source, exudates from purified germinating spores, which contain only compounds of AM fungal origin but have the disadvantage of producing extremely low concentrations of Myc factors.)

Biologically Active Compounds Present in AM Fungal Exudates are Amphiphilic

Mycorrhized root exudates were first extracted by a liquid-liquid procedure, with butanol and ethyl acetate. Aqueous, butanol and ethyl acetate phases were checked for biological activity with MtENOD11 and VsHab bioassays: activity was found in the butanol fraction which indicated that Myc factors are amphiphilic compounds. As shown in FIG. 1, an active compound could be detected with the MtENOD11 assay by a blue staining appearing on the growing roots, and with the VsHab assay by the appearance of clear branches close to the tip of vetch root hairs.

Then the butanol extract was submitted to Solid Phase Extraction (SPE) with a reverse phase C18 column and successively eluted with 20%, 50% and 100% acetonitrile solvent. Biological activity was found in the fraction eluted by 50% acetonitrile on MtENOD11 and VsHab assays confirming that the active compound(s) is amphiphilic. Similar results were obtained with more than five independent samples of mycorrhized root exudates. A very slight activity on VsHab could also be observed sometimes in the 100% acetonitrile eluate, suggesting that different compounds could be responsible for the MtENOD11 and the VsHab responses, the compound acting on the VsHab assay being slightly more hydrophobic than the compound acting on the MtENOD11 assay.

Exudates of germinating spores were extracted by the same liquid-liquid procedure with butanol and ethyl acetate. The activity on both MtENOD11 and VsHab assays was present only in the butanol phase. The same results were obtained with five independent samples of germinating spores. We can thus conclude that the amphiphilic compound(s) active on the MtENOD11 and VsHab assays are of AM fungal origin.

Two Types of Active Compounds in Mycorrhized Root Exudates

To further resolve the compounds active on MtENOD11 and VsHab and get information on their chromatographic properties, the butanol fraction had to be analyzed by HPLC. However, the mycorrhized root exudates being highly contaminated by plant root compounds and by phytagel, the butanol fraction was pre-treated by SPE before the HPLC step, as described in the preceding paragraph. The SPE fraction eluted by 50% acetonitrile, and active on the two bioassays, was then analyzed in a semi-preparative HPLC with a reverse phase C18 column and an acetonitrile-water gradient. Fourteen fractions were collected every two minutes. A typical profile is given in FIG. 2. Each fraction was tested for activity on MtENOD11 and VsHab. Fractions eluted at 30-48% of acetonitrile (ACN) (fraction A) were found to be active on MtENOD11, and fractions eluted at 64-72% of ACN (fraction B) were active on the VsHab bioassay. These data show that it is not the same compound which is active on both bioassays. The compound(s) active on MtENOD11 is more hydrophilic than the one(s) active on VsHab.

It is interesting to note that the elution characteristics of the fraction active on MtENOD11 correspond well to those observed with sulfated Nod factors of *Sinorhizobium meliloti* and *Rhizobium tropici* (33-45%), which can also exhibit activity with the MtENOD11 bioassay. On the other hand the elution characteristics of the fraction active on VsHab correspond well to those observed with non-sulfated Nod factor of *R. leguminosarum* bv. *viciae* (67%) and non-acetylated Nod factors of *Rhizobium meliloti* nodHnodL (66%) which can also exhibit activity with the vetch bioassay. These data are compatible with the hypothesis that the mycorrhized root exudates contain a mixture of sulfated and non-sulfated LCOs.

Two Types of Active Compounds in Germinating Spores Exudates

Butanol extracts from germinating spores exudates were analyzed in a semi-preparative HPLC in the same conditions as described above. As seen on FIG. 3, spore exudates also contained two types of active compounds, one more hydrophilic active on MtENOD11 (fraction A) and one more hydrophobic active on VsHab (fraction B). The elution characteristics of the two compounds are identical to those observed with the two active compounds from the mycorrhized root exudates. These results indicate that the two active compounds present in the mycorrhized root exudates are of AM fungal origin. Their chromatographic behavior and their biological activities are compatible with the hypothesis that they could correspond to sulfated and non-sulfated LCOs.

Modification of Activity Associated to Desulfatation of Fraction A

A mild methanolic hydrolysis of sulfated LCOs, as *S. meliloti* Nod factors, has been shown to remove the sulfate group without causing other structural modifications (Roche et al., 1991b). To check whether the biological activity on MtENOD11 of the fraction A collected after HPLC of butanol extracts from germinating spores exudates could be due to a sulfated LCO, a sample of fraction A was submitted to this mild hydrolysis treatment. The) treated fraction totally lost activity on MtENOD11 (see FIG. 4). Interestingly, whereas the fraction A was not originally active on the VsHab bioassay, the treated fraction exhibited a clear activity on VsHab (FIG. 4). That fraction A can after mild hydrolysis gain a function, the activity on VsHab, shows that this very mild methanolic hydrolysis has not drastically degraded the active compound of fraction A, but has simply modified it, probably by the removal of the sulfate moiety which is a very labile O-substitution in LCOs. These data indicate that the activity of fraction A on MtENOD11 could be due to sulfated LCO(s) and that the activity of the more hydrophobic fraction B on VsHab could be due to non-sulfated LCO(s).

EXAMPLE 2

Biochemical Characterization of MYC Factors

LC/MS and UPLC/MS

The different fractions obtained after the semi-preparative reversed phase HPLC of mycorrhized root extracts were individually chromatographed on an analytical reversed phase column under ultra-high pressure (UPLC). The detection occurred through ESI-MS.

Results are shown on FIGS. 5 to 8. These figures present the ion currents corresponding to LCOs supposed to be present in the samples, according to the HPLC and UPLC retention times, and biological activity. If there are compounds exhibiting the requested mass within their isotopic distribution, then they will appear on the chromatogram as peaks. As the peaks obtained in this manner could be artefactual (peaks might correspond to a minor compound of the isotopic profile), the corresponding spectra are also given in the lower part of each figure.

The first eight HPLC fractions, for which chromatographic behavior and biological activities suggested the presence of sulfated LCOs, were analyzed in the negative mode. According to the retention times measured in UPLC using standard tetrameric (DP4) and pentameric (DP5) LCOs, exact masses (error less then 10 ppm) corresponding to sulfated DP4 and DP5 entities were searched in the fraction 4 which showed the highest activity on the MtENOD11 assay. In this fraction, masses corresponding to sulfated DP4 bearing C16 acyls could easily be detected (FIG. 5). In agreement with their respective HPLC retention times, we were able to detect in the previous fraction (fraction 3) the corresponding DP5s (FIG. 7) and in the following (fraction 5) sulfated DP4 bearing C18 chains (FIG. 6). In the next fractions (6 to 8) DP3 entities have been researched without success. The compounds have been characterized first using different ion currents (fit between the called exact masses and the expected retention times) and secondly regarding the isotopic profile of the corresponding spectra. FIG. 8 illustrates the efficiency of the method to detect the presence or absence of a given compound, having a specific mass. Ion current m/z 1332.6, corresponding to a putative LCO(V,C18:2,S) produced only amplification of background noise (no individual well-defined peak), whereas the ion current m/z 1334.6 corresponding to a putative) LCO (V,C18:1,S) clearly demonstrated the presence of a UPLC peak containing a compound exhibiting the expected mass (data confirmed by the recorded mass spectrum). Thus the Myc extracts contain the pentameric sulfated LCO N-acylated by C18:1 but no derivative acylated by C18:2.

By using this procedure it was not possible to detect sulfated DP4 or DP5 entities carrying O-substitutions as acetyl, carbamoyl or fucosyl groups or N-substitution as a methyl group, that are very frequently found in the lipochito-oligosaccharidic Nod factors produced by diverse rhizobial strains.

Fractions 7 to 11 have been analyzed then on UPLC but the detection occurred in the positive ESI-MS mode. The same strategy was applied: ion call followed by analysis of the corresponding spectra.

Mycorrhized root extracts were also analyzed by LC/MS. Fractions eluting between 20 and 23 minutes on the semi-preparative HPLC were pooled, dried under nitrogen flux and redissolved in 150 μl of 50% ACN in water and 1% acetic acid. Solutions were directly infused into the ESI source of a Q-Tof Ultima spectrometer (Waters, US). Capillary was set at 3 kV, the cone voltage at 70V, the Rf lens at 35V. In the positive mode the molecular ions of two minor compounds at m/z 1045.5 and 1047.5 could be detected corresponding to the sodium cationized tetrameric LCOs bearing a C16:1 or a C16:2 acyl and no O-substitution. Masses and isotopic profiles confirmed the proposed structures.

As important amounts of contaminants (e.g. PEG) co-eluting with the searched non-sulfated LCO compounds in fractions 9-11 prevented their MS detection, a supplementary HPLC purification was performed. Fractions 9 and 10 of the semi-preparative HPLC were pooled and injected in an analytical C8 column and eluted using a gradient starting with 30% MeOH in water and finishing with 100% MeOH. Contaminants eluted from 1 to 15 minutes. The expected LCO compounds were awaited around 20 minutes. Fractions collected between 15 and 23 minutes were separately analyzed on UPLC-MS and detection of specific ions performed based on the observed corresponding sulfated species (DP4 and DP5; C16:0 and C18:1 acyl chains). Ion call of the exact mass m/z 1027.56 (DP4,C16:1) gave an answer in fraction eluting between 18 and 19 minutes. Retention time compared to synthetic standards and the exact mass and isotopic profile corresponded to the searched compound. The structure was definitively confirmed by the mass spectrum recorded, that exhibited the classic B fragmentation at m/z 400.2, 603.3, 806.4
MS/MS Demonstrating the presence of compounds having the adequate mass at the expected HPLC or UPLC retention time, is not sufficient to attest their structure. Therefore, we performed MS/MS analysis of one of the putative LCO compound. FIG. 9 presents the comparison between the *S. meliloti* sulfated Nod factor DP4 C16:2 in the negative mode MS/MS and the one recorded on the "Myc factor" candidate present in the sample, LCO(IV,C16:0,S). Characteristic ions of the reducing end at m/z 503 ($Y_2$), 605 and 706 ($Y_3$) are clearly detected in both case as well as the characteristic neutral loss of 101 amu (intracyclic rupture) starting from the molecular ion. The perfect fit between the two fragmentation patterns indicates the structural affiliation of the two molecules and indicates that the sulfate group is located on the reducing glucosamine residue whereas the fatty acyl substitution is localized on the terminal non-reducing glucosamine residue. Since fragmentation does not produce beta-elimination ions (fatty acid ions) it is very likely that the fatty acyl substitution is an amide on the N atom of the glucosamine residue.

EXAMPLE 3

Stimulation of Lateral Root Formation by MYC Factors

Butanol extract from mycorrhized root exudates, after further purification by solid phase extraction (SPE) and elution by 50% acetonitrile was incorporated into M plates and tested for growth of *M. truncatula* A17 seedlings. This purified Myc extract induced a significant stimulation of lateral root formation (P=0.05). When tested on a *M. truncatula* dmi1 mutant (Y6) this Myc extract did not stimulate lateral root formation, indicating that this semi-purified extract contained a Myc signal which activates lateral root formation (LRF) via the DMI symbiotic signaling pathway (FIG. 10A).

Germinating spores exudates were extracted with ethyl acetate and butanol. The three extracts (aqueous, ethyl acetate and butanol) were then checked for LRF stimulation on *M. truncatula* A17 seedlings. The butanol extract stimulated LRF significantly (P=0.05) whereas the aqueous and ethyl acetate extracts were not active (FIG. 10B). This experiment confirms the AM fungal origin of the amphiphilic compound(s) eliciting LRF stimulation.

The butanol extract of mycorrhized root exudates, after SPE, was further purified by semi-preparative HPLC and the fractions corresponding to sulfated LCOs (fraction A, active on the MtENOD11 assay) and to non-sulfated LCOs (fraction B, active on the VsHab assay) were collected separately and tested on *M. truncatula* A17 seedlings. The two fractions were found to significantly stimulate LRF (FIG. 10C). These data indicate that the Myc factors are made of a mixture of sulfated and non-sulfated simple LCOs that are both able to stimulate the formation of lateral roots in plants.

EXAMPLE 4

Effect of MYC Factors of AM Formation in the Model Legume *M. Truncatula*

Synthetic Myc factors produced by the cell factory approach, as described in Materials and Methods, were used to study the possible influence of Myc factors on mycorrhization of roots of the model legume *Medicago truncatula* by the AM fungus *Glomus intraradices*.

In a first series of experiments *M. truncatula* seedlings were grown in axenic conditions in test tubes on a slant gellified medium poor in phosphorus and nitrogen in which Myc factors were added at a concentration of $10^{-8}$ M. Each seedling was inoculated with 500 sterile fungal spores (Olah et al., 2005). The number of infection units (zones containing arbuscules, vesicles and internal hyphal networks) per plant was counted under a binocular magnifying glass six weeks after inoculation. Treatment by Myc factors increased the number of infection units per plant by 148% (see FIG. 11a).

In a second series of experiments *M. truncatula* seedlings were grown on a substrate made of charred clay granulates in non-sterile conditions and each seedling was inoculated with 50 fungal spores. Myc factors were added to the medium at a concentration of $10^{-8}$ M. The percentage of root colonization was measured by the grid intersect method three weeks after inoculation. The percentage of mycorrhized roots in plants treated by Myc factors was 28.5% higher than in the control plants (FIG. 11b).)

Conclusions: At low concentration ($10^{-8}$ M), synthetic Myc factors stimulate AM formation on the model legume *M. truncatula*, providing further evidence that the Myc factors that we have identified are genuine mycorrhizal signals.

The fact that Myc factors efficiently stimulate AM formation in legumes open the way to broad applications in horticulture (e.g. bean, chickpea, lentil), agriculture (e.g. soybean, pea, faba bean, alfalfa, peanut) and forestry (e.g. black locust).

EXAMPLE 5

Effect of MYC Factors on Legume Root Development

AM fungi secrete diffusible compounds which stimulate lateral root formation (LRF) in the model legume *Medicago truncatula* (Olah et al., 2005). We have shown (see Example 3) that HPLC fractions containing fungal sulfated and non-sulfated LCOs elicit this LRF stimulation. To demonstrate that this stimulation of LRF is really due to LCOs and not to fungal contaminating compounds possibly present in these HPLC fractions, we used the synthetic sulfated and non-sulfated LCOs, having the same structure as those detected in fungal exudates (see Example 4 and Materials and Methods).

At $10^{-8}$ M pure synthetic sulfated Myc factors, or pure non-sulfated factors, as well as a mixture of both sulfated and non-sulfated Myc factors, were all clearly stimulating LRF (see FIG. 12a) showing that both types of compounds act as plant growth regulators. In contrast, at $10^{-10}$ M the mixture of sulfated and non-sulfated Myc factors was still extremely active whereas the pure compounds, sulfated or not, were not active. These data show that a mixture of sulfated and non-sulfated Myc factors is clearly more active than pure sulfated or non-sulfated Myc factors.

Thus Myc factors are not only symbiotic signals activating the symbiotic program of the host plant during early steps of mycorhization, they can also act as genuine plant regulators, stimulate lateral root formation and influence root architecture.

From an agricultural point of view, it was important to address the question of the possible influence of Myc factors not only on root branching but also on the global development of the root system. After growing plant seedlings for 8 days on the growth medium containing or not a mixture of sulfated and non-sulfated Myc factors, roots were cut, scanned and the root system was analyzed with the WinRhizo software. Treatment with Myc factors resulted in a 13.16% increase of total root length (FIG. 12b). Treatment with Myc factors is thus able to stimulate development of the whole root system.

Conclusions: Both sulfated and non-sulfated Myc factors are active signals, acting at a low concentration ($10^{-8}$ M), but a mixture of sulfated and non-sulfated Myc factors is clearly more active (down to $10^{-10}$ M).

They effectively stimulate lateral root formation and root system development and are therefore not only symbiotic signals but also potent plant growth regulators.

These findings open the way of using these molecules in horticulture, agriculture and forestry to stimulate plant root development and plant growth.

EXAMPLE 6

MYC Factors Elicit Plant Responses via the DMI Symbiotic Signaling Pathway

A symbiotic signaling pathway has been identified in *M. truncatula* with genes coding for Nod factor perception (NFP), for calcium signaling (DMI1, DMI2 and DMI3) and a nodulation specific transcription activator (NSF1) (Catoira et al., 2000; Smit et al., 2005). Mutations in genes DMI1, DMI2 and DMI3 result in the alteration of nodule formation but also of mycorrhiza formation, indicating that these three DMI genes are involved in a signalling pathway common to nodulation and mycorrhization (Catoira et al., 2000). In contrast, mutations in the NSP1 gene result in a defect in nodulation but mycorrhization is unaffected (Catoira et al., 2000). This finding has led to the hypothesis that mycorrhizal symbiotic signals, Myc factors, are activating the plant mycorrhizal programme via the DMI pathway (Catoira et al., 2000). It is impossible to determine whether the DMI genes are involved in the stimulation of AM formation by Myc factors because dmi mutants are defective for mycorrhiza formation. To address the question of the possible involvement of plant symbiotic genes in the response to Myc factors we have thus used the *M. truncatula* lateral root formation (LRF) assay described in Examples 3 and 5.

Sulfated Myc factors exhibit some structural similarities with *Sinorhizobium meliloti* Nod factors. To avoid possible cross talk between Nod factor and Myc factor signaling we used non-sulfated synthetic Myc factors. We studied the LRF stimulation response in the *M. truncatula* wild-type A17 line as a control, and in dmi1 (Y6), dmi2 (TR25), dmi3 (TRV25) and nsp1 (B85) mutants.

As already described in Example 5, treatment of the wild-type line with $10^{-8}$M non-sulfated Myc factors resulted in a clear stimulation of lateral root formation. In contrast, in the mycorrhiza defective dmi1, dmi2 and dmi3 mutants, Myc factors did not trigger LRF stimulation (see FIG. 13). In the nsp1 mutant which is nodulation-defective but has a normal mycorrhizal phenotype, and in which Nod factors are unable to stimulate LRF, Myc factors triggered a very clear LRF stimulation (FIG. 13). These data show that Myc factors elicit plant responses downstream of the DMI genes via a mycorrhiza specific signaling pathway, distinct from the Nod factor signaling pathway (NSP1).

Conclusions:

The ability of Myc factors to stimulate LRF is abolished in dmi1, dmi2 and dmi3 mutants. This shows that the developmental responses induced by Myc factors are elicited via the DMI symbiotic pathway, further demonstrating that Myc factors are genuine symbiotic signals.

The nodulation-specific NSP1 gene is not required for the LRF stimulation response, indicating that Myc factors trigger this developmental response via a Myc specific pathway acting through and downstream of DMI genes and independent of the nodulation specific pathway (NSP1). This is further evidence that the Myc factors that we have identified) are genuine mycorrhizal signals.

EXAMPLE 7

Stimulation of AM Formation in Excised Transformed Roots of Carrot, a System used for the Production of Industrial Mycorrhizal Inoculants AM fungi are obligate symbionts: they cannot propagate and form spores in pure culture. For their growth they need to colonize roots of host plants. This strict requirement has hampered both basic research on AM symbiosis and the possibility of producing AM fungal inoculants on a large scale for horticultural and agricultural purposes. An important breakthrough was achieved by using cultures of excised transformed roots to grow AM fungi, making possible the production of large quantities of sterile fungal spores (Bécard and Fortin, 1988). A system which has been used for many years (Chabot et al., 1992) is the co-cultivation of the AM fungus *Glomus intraradices* strain DAOM 197198 with a carrot excised root clone transformed by *Agrobacterium rhizogenes*. This co-cultivation system is used namely by the Biotech company PremierTech (Québec) for the production of commercial AM fungal inoculants. We have addressed the question of whether the use of Myc factors at low concentrations, as an additive in growth media, could stimulate mycorrhization of excised roots.

We first used a mixture of sulfated and non-sulfated Myc factors, produced by appropriate rhizobial mutants (see Materials and Methods), which was added to the growth medium at a concentration of $10^{-8}$M. Axenic excised carrot roots were inoculated with sterile spores of *G. intraradices*. The percent of root length colonized by the AM fungus was estimated by the grid line intersect method (Giovannetti and Mosse (1980). Five repetitions were used. Reading was performed with a binocular magnifying glass after eight weeks, in a double blind way.

On FIG. 14a it can be seen that the addition of a mixture of sulfated and non-sulfated Myc factors at $10^{-8}$ M in the growth medium resulted in a very strong increase in the percent of colonization (+68.6%).

In a second experiment a mixture of sulfated and non-sulfated synthetic Myc factors was added to the growth medium at $10^{-8}$ M. Fifteen repetitions were used. As shown on FIG. 14b after eight weeks the effect of Myc factors on the stimulation of AM formation was quite significant (+20.5%).
Conclusions:
A mixture of sulfated and non-sulfated Myc factors actively stimulates AM formation in the roots of the non-legume carrot. This is further evidence that the Myc factors that we have identified and that have been synthesized are genuine mycorrhizal signals.

Both synthetic Myc factors prepared by a biochemical procedure and Myc factors prepared from mutant rhizobial strains are effective at stimulating mycorrhiza formation showing that these two types of strategies are suitable for large-scale production of Myc factors.

These data open the way to using Myc factors as additives in the growth media utilised for AM inoculant production by the biotech industry, using excised transformed roots.

EXAMPLE 8

Effect of MYC Factors on AM Formation in the Non-Legume *Tagetes patula*

*Tagetes patula*, member of the Asteraceae family, has been chosen as a non-legume host plant. *T. patula* (French marigold) is a very popular garden plant. This species is used in companion planting for many vegetable crops. Its root secretions are reported to kill nematodes in the soil and it is said to repel harmful insects, such as white fly amongst tomatoes. The whole plant can be harvested when in flower and distilled for its essential oil which is used in perfumery. *T. patula* is used for testing mycorrhization because it is a small plant easy to handle and exhibiting rapid root colonization by AM fungi. The "Légion d'honneur" variety was used. Mycorrhization assays were performed by growing seedlings on a substrate made of particles of charred clay. Seedlings were inoculated with sterile spores of *G. intraradices*, and Myc factors were added at the concentration of $10^{-8}$ M.

In a first series of experiment a mixture of sulfated and non-sulfated synthetic Myc factors was used. The degree of mycorrhization was estimated four weeks after inoculation by counting the number of infection units. Myc factor-treated plantlets had a highly significant 153.5% increase of the number of infection units per plant (FIG. 15a1). Myc factors could increase the number of infection sites either by stimulating the root system development or by increasing the density of infection. Indeed the treatment by Myc factors resulted in both a 49.1% increase of the root length (FIG. 15a2), and a 30.9% increase of the infection density (FIG. 15a3).

In a second experiment, inoculated plants were treated either with pure sulfated or non-sulfated Myc factors, or with a mixture of both. Four weeks after inoculation the colonization rate was estimated by the grid intersect method. Results are represented in FIG. 15b. Treatment with a mixture of sulfated and non-sulfated Myc factors elicited a significant doubling of the root colonization rate (+104.5%), whereas pure sulfated and pure non-sulfated Myc factors resulted in 42.3% and 75.4% increases respectively.
Conclusions:

Myc factors stimulate AM formation in a non-legume plant, further evidence that the Myc factors that we have identified are genuine mycorrhizal signals.

Both sulfated and non-sulfated Myc factors are active, but the mixture of both is clearly more active.

The fact that Myc factors efficiently stimulate AM formation and root development in a non-legume opens the way to extremely broad applications in horticulture, agriculture and forestry.

EXAMPLE 9

Effect of MYC Factors on Seed Germination of a Non-Legume, Tomato

In previous examples, we have shown that Myc factors are not only symbiotic signals that activate the plant mycorrhizal program, but can also act as plant growth regulators and stimulate root system development at a very early stage of seedling development. We have thus investigated the possible influence of Myc factors on seed germination on a non-legume plant. The tomato variety Heinz 1706 has been chosen because this line is well characterized and was selected for the US tomato genome sequencing project. In addition, affymetrix microarrays are available making possible gene expression profiling studies with this tomato line.

For these studies purified synthetic Myc factors were used, either sulfated, non-sulfated or a mixture of both. Myc factors were added to germination agar medium and poured into Petri dishes. Seeds were laid at the surface of agar plates and incubated in the dark at 14° C., 20° C. and 28° C. The percentage of germination was scored everyday.

Experiments were performed with seeds which had been vernalized by storing at 4° C. for at least eight weeks. The presence of Myc factors in the germination medium, in the $10^{-8}$ M to $10^{-10}$ M range, resulted in a very clear stimulation of germination at 14° C. and 20° C. (see FIG. 16). Each type of Myc factors, sulfated or non-sulfated, was active, but interestingly the mixture of both types was clearly more active. No significant effect of Myc factors on germination could be detected at the highest temperature, 28° C. (data not shown). These data suggest that this stimulation effect is operating at temperatures which correspond to the range of common soil temperatures. We can hypothesize that plants and their AM fungal symbionts have co-evolved not only for the formation of mycorrhiza in the developing roots, but also at a very early stage of their interactions, germination. Both partners could have the advantage of linking the efficiency of seed germination and early root development to the presence of the fungal partner. Stimulation of germination was associated with a subsequent better seedling development as shown in FIG. 16b.

The fact that seeds respond to Myc factors shows that plant components required for Myc factor perception (receptors) and transduction are present and functional in seeds. This finding opens the way to seed treatment of crops with Myc factors in agricultural conditions. The observation that Myc factors are active on seed germination at extremely low concentrations ($10^{-10}$ M) opens the way to seed treatment technology of a low cost (low requirement for active material) and respecting environment (use of extremely low concentrations of natural compounds).

Conclusions:

Both sulfated and non-sulfated Myc factors stimulate seed germination of tomato, a non-legume plant, but the mixture of both is clearly more active. These two types of Myc factors are therefore not only symbiotic signals but also potent plant growth regulators acting in both legumes and non-legumes.

From an agricultural point of view, these results open the way to important applications in horticulture, agriculture and forestry: seed treatment by Myc factors, preferably a mixture of both sulfated and non-sulfated ones, could improve the percentage and rate of germination and stimulate the development of young seedlings for most cultivated plants, the majority of which are able to establish this endomycorrhizal symbiosis.

REFERENCES

Akiyama K, Matsuzaki K, Hayashi H (2005) Plant sesquiterpenes induce hyphal branching in arbuscular mycorrhizal fungi. *Nature*, 435: 824-827.

Andriakaja A, Boisson-Dernier A, Frances L, Sauviac L, Jauneau A, Barker D G, Carvalho-Niebel F (2007) AP2-ERF transcription factors mediate Nod factor dependent Mt ENOD11 activation in root hairs via a novel cis-regulatory motif. *Plant Cell*, 19:2866-2885.

Ardourel M, Demont N, Debelle F, Maillet F, de Billy F, Promé J C, Dénarié J, Truchet G (1994) *Rhizobium meliloti* lipooligosaccharide nodulation factors: Different structural requirements for bacterial entry into target root hair cells and induction of plant symbiotic developmental responses. *Plant Cell*, 6:1357-1374.

Bécard G, Fortin J A (1988) Early events of vesicular-arbuscular mycorrhiza formation in Ri T-DNA transformed roots. *New Phytol.*, 108:211-218.

Benamor B, Shaw S, Oldroyd G, Maillet F, Penmetsa R V, Cook D, Long S, Dénarié J, Gough C (2003). The NFP locus of *Medicago truncatula* controls an early step of Nod factor signal transduction upstream of a rapid calcium flux and root hair deformation. *Plant J.*, 34: 495-506.

Besserer A, Puech-Pagès V, Kiefer P, Gomez-Roldan V, Jauneau A, Roy S, Portals J C, Roux C, Bécard G, Séjalon-Delmas N (2006) Strigolactones stimulate arbuscular mycorrhizal fungi by activating mitochondria. *PLoS Biol.*, 4(7):e226.

Catoira R, Galera C, De Billy F, Penmetsa R V, Journet E P, Maillet F, Rosenberg C, Cook D, gough C, Dénarié J (2000) Four genes of *Medicago truncatula* controlling components of a Nod factor transduction pathway. *Plant Cell*, 12: 1647-1666.

Chabot S, Bécard G, Piché Y (1992) The life cycle of *Glomus intraradices* in root organ culture. *Mycologia*, 84: 315-321.

Demont N, Debellé F, Aurelle H, Dénarié J, Promé J C (1993) Role of the *Rhizobium meliloti* nodF and nodE genes in the biosynthesis of lipo-oligosaccharidic nodulation factors. *J. Biol. Chem.*, 268: 20134-20142.

Dénarié J, Debellé F, Promé J C (1996) *Rhizobium* lipo-chitooligosaccharide nodulation factors: signaling molecules mediating recognition and morphogenesis. *Annu. Rev. Biochem.*, 65: 503-535.

D'Haeze W, Holsters M (2002) Nod factor structures, responses, and perception during initiation of nodule development. *Glycobiology*, 12: 79R-105R.

Doner L W, Bécard G (1991) Solubilization of gellan gels by chelation of cations. *Biotechnol Tech.*, 1991; 5:25-28.

Giovanetti M, Mosse B (1980) An evaluation of techniques for measuring vesicular-arbuscular mycorrhizal infection in roots. *New Phytologist*, 84:489-500.

Grenouillat N, Vauzeilles B, Bono J J, Samain E, Beau J M. (2004) Simple synthesis of nodulation-factor analogues exhibiting high affinity towards a specific binding protein. *Angew Chem Int Ed Engl.*, 43:4644-4646.

Harrison M (2005) Signaling in the arbuscular mycorrhizal symbiosis. *Annu. Rev. Microbiol.*, 59: 19-42.

Hewitt, E. J (1966) Sand and water culture methods used in the study of plant nutrition. Technical Communication No. 22 (revised 2nd edn). *Com. Bur. of Horticul. and Plant Crops* East Malling, Maidstore, Kent, UK.

Journet E P, El-Gachtouli N, Vemoud V, de Billy F, Pichon M, Dedieu A, Arnould C, Morandi D, Barker D, Gianinazzi-Pearson V (2001) *Medicago truncatula* ENOD11: a novel RPRP-encoding early nodulin gene expressed during mycorrhization in arbuscule-containing cells. *Mol. Plant Microbe Interact.*, 14: 737-748.

Kosuta S, Chabaud M, Lougnon G, Gough C, Dénarié J, Barker D G, Bécard G (2003) A diffusible factor from arbuscular mycorrhizal fungi induces symbiosis-specific MtENOD11 expression in roots of *Medicago truncatula*. *Plant Physiol.*, 131: 952-962.

Navazio L, Moscatiello R, Genre A, Novero M, Baldan B, Bonfante P, Mariani P (2007) A diffusible signal from arbuscular mycorrhizal fungi elicits a transient cytosolic calcium) elevation in host plant cells. *Plant Physiol.* 144: 673-681.

Olah B, Brière C, Bécard G, Dénarié J, Gough C (2005) Nod factors and a diffusible factor from arbuscular mycorrhizal fungi stimulate lateral root formation in *Medicago truncatula* via the DMI1/DMI2 signalling pathway. *Plant J.*, 44: 195-207.

Ohsten Rasmussen M, Hogg B, Bono J J, Samain E, Driguez H (2004) New access to lipo-chitooligosaccharide nodulation factors. *Org. Biomol. Chem.*, 2: 1908-1910.

Price N P J, Relic B, Talmont F, Lewin A, Promé D, Pueppke S G, Maillet F, Dénarié J, Promé J C, Broughton W J (1992) Broad-host-range *Rhizobium* species strain NGR234 secretes a family of carbamoylated, and fucosylated, nodulation signals that are O-acetylated or sulphated. *Mol. Microbiol.*, 23: 3575-3584.

R Development Core Team (2009) R: A language and environment for statistical computing. R Foundation for Statistical Computing, Vienna, Austria. ISBN 3-900051-07-0, URL http://www.R-project.org.

Remy W, Taylor T N, Hass H, Kerp H (1994) Four hundred-million-year-old vesicular arbuscular mycorrhizae. *Proc. Natl. Acad. Sci. USA*, 91: 11841-43.

Roche P, Debellé F, Maillet F, Lerouge P, Faucher C, Truchet G, Dénarié J, Promé J C (1991a) Molecular basis of symbiotic host specificity in *Rhizobium meliloti*: nodH and nodPQ genes encode the sulfation of lipo-oligosaccharide signals. *Cell*, 67: 1131-1143.

Roche P, Lerouge P, Ponthus C, Promé J C (1991b) Structural determination of bacterial nodulation factors involved in the *Rhizobium meliloti*-alfalfa symbiosis. *J. Biol. Chem.*, 266: 10933-10940.

Samain E, Drouillard S, Heyraud A, Driguez H, Gram-scale synthesis of recombinant chitooligosaccharides in *Escherichia coli*. *Carbohydrate Research*, 302: 35-42.

Samain E, Chazalet V, Geremia R A (1999), Production of O-acetylated and sulphated chitooligosaccharides by recombinant *Escherichia coli* strains harboring different combinations of nod genes. *Journal of Biotechnology*, 72: 33-47.

Smit P, Raedts J, Portyanko V, Debellé F, Gough C, Bisseling T, Geurts R (2005) NSP1 of the GRAS protein family is essential for rhizobial Nod factor-induced transcription. *Science*, 308:1789-91.

Smith S E, Read D J (2008) Mycorrhizal symbiosis. 787 pp., Academic Press.

Stacey G, Libault M, Brechenmacher L, Wan J, May G (2006) Genetics and functional genomics of legume nodulation. *Curr. Opin. Plant Biol.*, 9:110-121.

Spaink H P, Wijfjes A H M, van der Drift K M G M, Haverkamp J, Thomas-Oates J E, Lugtenberg B J J (1994) Structural identification of metabolites produced by the NodB and NodC proteins of *Rhizobium leguminosarum*. *Mol. Microbiol.*, 13:821-831.

Spaink H P, Wijfjes A H M, Lugtenberg B J J (1995) *Rhizobium* NodI and NodJ proteins play a role in the efficiency of secretion of lipochitin oligosaccharides. *J. Bacteriol.*, 177: 6276-6281.

Vierheilig H, Coughlan A P, Wyss U, Piché Y (1998) Ink and vinegar, a simple staining technique for arbuscular-mycorrhizal fungi. *Appl. Environm. Microbiol.*, 64:5004-5007.

Weidmann S, Sanchez L, Descombin J, Chatagnier O, Gianinazzi S, Gianinazzi-Pearson V (2004) Fungal elicitation of signal transduction-related plant genes precedes mycorrhiza establishment and requires the dmi3 gene in *Medicago truncatula*. *Mol. Plant Microbe Interact.*, 17: 1385-1393.

The invention claimed is:

1. A method for stimulating mycorrhization of a plant which comprises the steps of:

contacting a plant, plant part, seedling or seed thereof with one or more lipochitooligosaccharide defined by formula (I):

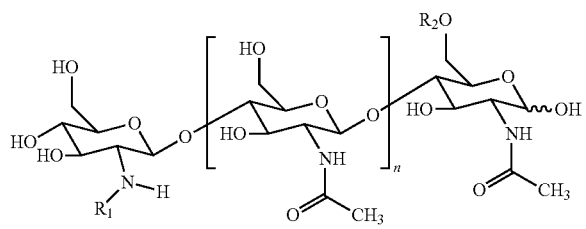

wherein n is 2 or 3, $R_1$ represents a saturated or monounsaturated fatty acid chain containing 16 or 18 carbon atoms, and $R_2$ represents H or $SO_3H$; and contacting said plant, plant part, seedling or seed thereof with an arbuscular mycorrhizal fungus.

2. The method of claim 1, wherein the one or more lipochitooligosaccharide is selected from a lipochitooligosaccharide of formula (I) wherein $R_1$ represents a saturated or monounsaturated fatty acid chain containing 18 carbon atoms, and $R_2$ represents H or $SO_3H$.

3. The method of claim 2, wherein $R_1$ is a monounsaturated fatty acid chain containing 18 carbon atoms.

4. The method of claim 1 wherein $R_1$ represents a saturated or monounsaturated fatty acid chain containing 18 carbon atoms, and $R_2$ represents H.

5. The method of claim 1 wherein $R_1$ represents a monounsaturated fatty acid chain containing 18 carbon atoms and $R_2$ represents H.

6. The method of claim 1, wherein the one or more lipochitooligosaccharide of formula (I) is used at a concentration of $10^{-5}$ to $10^{-12}$ M.

7. The method of claim 1, wherein the one or more lipochitooligosaccharide of formula (I) is used at a concentration of $10^{-7}$ to $10^{-10}$ M.

8. The method of claim 1, wherein the plant is a legume.

9. The method of claim 1, wherein the plant is a non-legume.

10. The method of claim 1, wherein root system development of the plant is stimulated after said steps.

11. The method of claim 1, wherein mycorrhization of the plant is stimulated after said steps.

12. The method of claim 1, wherein the one or more lipochitooligosaccharide is an additive for production of an arbuscular mycorrhizal inoculant.

13. A method for stimulating mycorrhization of a plant which comprises the steps of:

contacting a plant, plant part, seedling or seed thereof with mixture of lipochitooligosaccharides defined by formula (I):

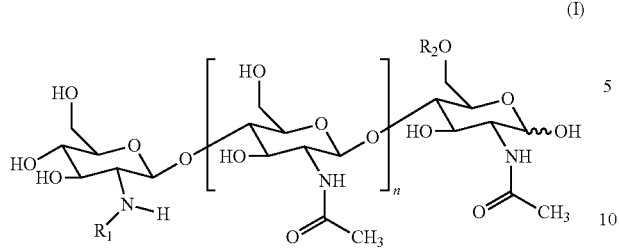

wherein n is 2 or 3, $R_1$ represents a saturated or monounsaturated fatty acid chain containing 16 or 18 carbon atoms, and $R_2$ represents H or $SO_3H$; and contacting said plant, plant part, seedling or seed thereof with an arbuscular mycorrhizal fungus, wherein the mixture of a lipochitooligosaccharides comprises a lipochitooligosaccharide wherein $R_2$ represents H, and a lipochitooligosaccharide wherein $R_2$ represents $SO_3H$ is uccd.

14. The method of claim 13, wherein said mixture comprises a lipochitooligosaccharide of formula (I) wherein n=2, $R_1$ represents a saturated or monounsaturated fatty acid chain containing 18 carbon atoms, and $R_2$ represents H, and at least one lipochitooligosaccharide selected from:
  (a) a lipochitooligosaccharide of formula (I) wherein n=2, $R_1$ represents a saturated or monounsaturated fatty acid chain containing 18 carbon atoms, and $R_2$ represents $SO_3H$;
  (b) a lipochitooligosaccharide of formula (I) wherein n=2, $R_1$ represents a saturated or monounsaturated fatty acid chain containing 16 carbon atoms, and $R_2$ represents $SO_3H$;
  (c) a lipochitooligosaccharide of formula (I) wherein n=3, $R_1$ represents a saturated or monounsaturated fatty acid chain containing 18 carbon atoms, and $R_2$ represents $SO_3H$; or
  (d) a lipochitooligosaccharide of formula (I) wherein n=3, $R_1$ represents a saturated or monounsaturated fatty acid chain containing 16 carbon atoms, and $R_2$ represents $SO_3H$.

15. The method of claim 14, wherein said mixture further comprises at least one lipochitooligosaccharide selected from:
  (a) a lipochitooligosaccharide of formula (I) wherein n=2, $R_1$ represents a saturated or monounsaturated fatty acid chain containing 16 carbon atoms, and $R_2$ represents H;
  (b) a lipochitooligosaccharide of formula (I) wherein n=3, $R_1$ represents a saturated or monounsaturated fatty acid chain containing 16 carbon atoms, and $R_2$ represents H; or
  (c) a lipochitooligosaccharide of formula (I) wherein n=3, $R_1$ represents a saturated or monounsaturated fatty acid chain containing 18 carbon atoms, and $R_2$ represents H.

16. A method for stimulating root system development of a plant which comprises contacting a plant, plant part, seedling or seed thereof with a mixture of a lipochitooligosaccharide of formula:

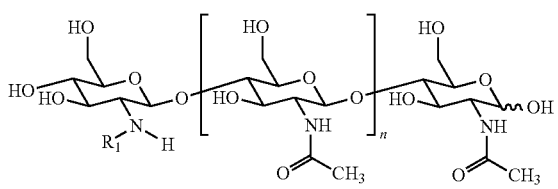

and a lipochitooligosaccharide of formula:

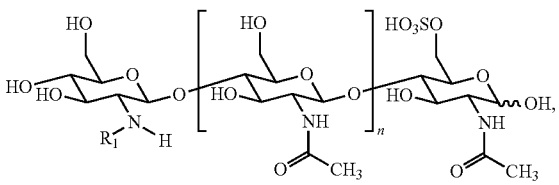

wherein n is 2 or 3 and $R_1$ represents a saturated or monounsaturated fatty acid chain containing 16 or 18 carbon atoms.

17. The method of claim 16, wherein the plant is a non-legume plant.

* * * * *